US012741038B2

(12) United States Patent
Irving et al.

(10) Patent No.: US 12,741,038 B2
(45) Date of Patent: Sep. 22, 2026

(54) MAGNETIC FORMULATIONS FOR BIOMARKER SAMPLING AND ENHANCED DRUG DELIVERY

(71) Applicant: Rocket Science Health Corp., Victoria (CA)

(72) Inventors: Kenneth Irving, Victoria (CA); Timothy Rees, Victoria (CA); Hilary Egglestone, Victoria (CA); Sape De Vries, Victoria (CA); Nigel John Fairbank, Jr., Victoria (CA); Alec Lillis, Victoria (CA)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 19/386,884

(22) Filed: Nov. 12, 2025

(65) Prior Publication Data

US 2026/0061081 A1 Mar. 5, 2026

Related U.S. Application Data

(63) Continuation of application No. PCT/CA2024/051611, filed on Dec. 3, 2024.

(60) Provisional application No. 63/606,080, filed on Dec. 4, 2023.

(51) Int. Cl.
*A61K 49/18* (2006.01)
*A61B 10/00* (2006.01)

(52) U.S. Cl.
CPC ...... *A61K 49/1875* (2013.01); *A61B 10/0045* (2013.01); *A61B 2010/0077* (2013.01)

(58) Field of Classification Search
None
See application file for complete search history.

(56) References Cited

U.S. PATENT DOCUMENTS

| | | | | |
|---|---|---|---|---|
| 6,200,547 | B1 | 3/2001 | Volkonsky et al. | |
| 2012/0149029 | A1 * | 6/2012 | Flynn ..................... | A61B 90/39 435/7.1 |
| 2012/0184941 | A1 | 7/2012 | Levy et al. | |
| 2013/0267762 | A1 | 10/2013 | Levy et al. | |
| 2019/0293638 | A1 | 9/2019 | Krug | |
| 2020/0188537 | A1 * | 6/2020 | Flynn ..................... | A61N 1/406 |
| 2022/0409871 | A1 | 12/2022 | Shpigelmacher et al. | |

FOREIGN PATENT DOCUMENTS

| | | | | |
|---|---|---|---|---|
| EP | 3866981 A1 | | 8/2021 | |
| WO | WO 20/217097 | * | 10/2020 | ............. G01N 33/48 |
| WO | 2025118073 A1 | | 6/2025 | |

OTHER PUBLICATIONS

International Search Report and Written Opinion received in PCT Application No. PCT/CA2024/051611, mailed on Jan. 24, 2025, 18 pages.
Oudart et al. (2017) "Tau Protein as a Possible Marker of Cerebrospinal Fluid Leakage in Cerebrospinal Fluid Rhinorrhoea: A Pilot Study", Biochemia Medica, 27(3):030703:5 pages.

* cited by examiner

*Primary Examiner* — Allison M Fox
(74) *Attorney, Agent, or Firm* — Mintz Levin Cohn Ferris Glovsky and Popeo PC

(57) ABSTRACT

The present disclosure describes formulations, methods, and devices tor biomarker sampling and therapeutic delivery using magnetic formulations. When combined with the application of external magnetic fields, magnetic formulations move within the nasal cavity. Magnetic formulations provide benefits including the ability to: target or steer placement of the formulations via a magnetic field, enhance mixing of the formulation via a magnetic field, enhance biological material collection via antibody-coated magnetic beads, or enhance sample retrieval via a magnetic-tipped inserter. Example biological materials for collection include proteins, enzymes, neural stem cells, and other biomarkers.

13 Claims, 17 Drawing Sheets

MAGNETIC FORMULATIONS FOR BIOMARKER SAMPLING AND ENHANCED DRUG DELIVERY

CROSS REFERENCE

This application is a continuation of International Application No. PCT/CA2024/051611, filed Dec. 3, 2024, which claims the benefit to U.S. Provisional Application No. 63/606,080 filed Dec. 4, 2023, the contents of each are incorporated herein by reference.

BACKGROUND

The human nasal cavity is a region of interest for both biomarker sampling and for therapeutic delivery. Intranasal delivery of sampling and therapeutic formulations allows for interaction with targeted regions of the nasal cavity such as the olfactory region. For certain applications, it is advantageous to precisely control contact between a formulation delivered within the nasal cavity and the targeted region of the nasal cavity. There is a need for formulations, methods, and devices to enhance intranasal biomarker sampling and therapeutic delivery. Additionally, there is a need for formulations, methods, and devices to enhance biomarker sampling and therapeutic delivery targeting other body surfaces.

SUMMARY

It is appreciated by the inventors that challenges related to intranasal biomarker sampling and therapeutic delivery include difficulties related to insufficient contact between a formulation delivered within the nasal cavity and the targeted region of the nasal cavity. In one aspect, provided herein, is a method of collecting biological material from an intranasal region of a subject, the method comprising: delivering a magnetic formulation comprising a plurality of magnetic particles to an intranasal region of a subject, wherein the magnetic formulation is configured to capture the biological material; and retrieving at least a portion of the magnetic formulation from the intranasal region, thereby collecting any biological material captured by the portion of the magnetic formulation. In some embodiments, the intranasal region is an olfactory region of the subject or a targeted sub-region of the nasal cavity. In some embodiments, the biological material is captured from cerebrospinal fluid (CSF). In some embodiments, analysis of the collected biological material provides a quantitative value for a concentration of tau protein, a concentration of beta-amyloid, or a ratio thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description and accompanying drawings, that set forth illustrative embodiments in which the principles of the present disclosure are utilized.

DETAILED DESCRIPTION

Figure 1:
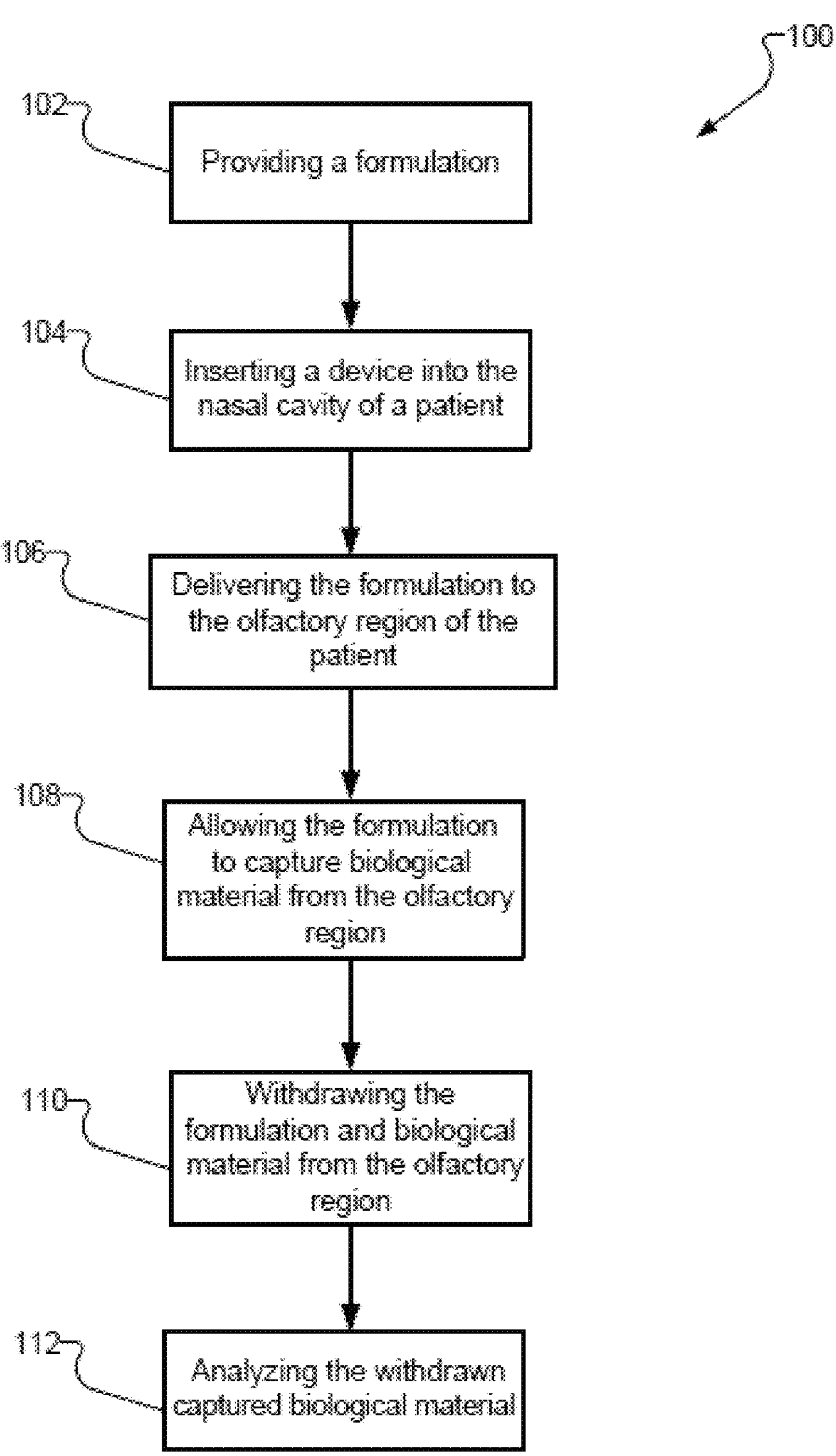
FIG. 1 depicts a flow chart showing the steps in a method for collecting biological material according to one embodiment.

This disclosure provides formulations, methods, and devices for intranasal biomarker sampling and therapeutic delivery using magnetic formulations. When combined with the application of external magnetic fields, magnetic formulations move within the nasal cavity. Intranasal magnetic formulations provide benefits including the ability to: target or steer placement of the formulations via a magnetic field, enhance intranasal mixing of the formulation via a magnetic field, enhance protein collection via antibody-coated magnetic beads, or enhance sample retrieval via a magnetic-tipped inserter.

In some embodiments, a method of collecting biological material from an intranasal region of a subject comprises: delivering a magnetic formulation comprising a plurality of magnetic particles to an intranasal region of a subject, wherein the magnetic formulation is configured to capture the biological material; and retrieving at least a portion of the magnetic formulation from the intranasal region, thereby collecting any biological material captured by the portion of the magnetic formulation. In some embodiments, the intranasal region is an olfactory region of the subject. In some embodiments, the intranasal region is a targeted sub-region of the nasal cavity.

In some embodiments, the magnetic particles are paramagnetic, diamagnetic, or ferromagnetic. In some embodiments, the biological material is captured from cerebrospinal fluid (CSF). In some embodiments, the magnetic particles are non-coated. In some embodiments, the magnetic particles are coated with or coupled to one or more antibodies configured to bind to a selected biological material. In some embodiments, each magnetic particle is coated with or coupled to a single antibody. In some embodiments, each magnetic particle is coated with or coupled to multiple antibodies.

In some embodiments, analysis of the captured biological material provides a quantitative value for a concentration of tau protein, a concentration of beta-amyloid, or a ratio thereof. In some embodiments, analysis of the captured biological material provides a quantitative value for a ratio of tau protein and beta-amyloid 42, thereby enabling a diagnosis of Alzheimer's disease. In some embodiments, the method additionally comprises eluting the captured biological material from the magnetic particles, and then analyzing the eluted biological material. In some embodiments, the biological material is analyzed via an enzyme-linked immunosorbent assay (ELISA).

In some embodiments, the method additionally comprises analyzing the captured biological material as a protein-bead complex. In some embodiments, the magnetic particles or protein-bead complex is washed and/or frozen prior to analysis of the captured biological material. In some embodiments, the biological material is analyzed via a self-administered test. In some embodiments, the biological material is analyzed via a lateral flow assay, a lateral flow immunoassay, a lateral flow immunochromatographic assay, or a magnetic lateral flow analyzer instrument.

In some embodiments, the portion of the magnetic formulation is retrieved using a magnet. In some embodiments, the method additionally comprises exposing the subject to a magnetic field prior to retrieving at least a portion of the magnetic formulation. In some embodiments, the magnetic field is an oscillating magnetic field. In some embodiments, a frequency of the oscillating magnetic field may be about 0.01-0.02, about 0.02-0.03, about 0.03-0.04, about 0.04-0.05, about 0.05-0.06, about 0.06-0.07, about 0.07-0.08, about 0.08-0.09, about 0.09-0.1, about 0.1-0.15, about 0.15-0.2, about 0.2-0.25, about 0.25-0.3, about 0.3-0.35, about 0.35-0.4, about 0.4-0.45, about 0.45-0.5, about 0.5-0.55, about 0.55-0.6, about 0.6-0.65, about 0.65-0.7, about 0.7-0.75, about 0.75-0.8, about 0.8-0.85, about 0.85-0.9, about 0.9-0.95, about 0.95-1, about 1-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, about 95-100, about 100-110, about 110-120, about 120-130, about 130-140, about 140-150, about 150-160, about 160-170, about 170-180, about 180-190, about 190-200, about 200-220, about 220-240, about 240-260, about 260-280, about 280-300, about 300-350, about 350-400, about 400-450, about 450-500, about 500-550, about 550-600, about 600-650, about 650-700, about 700-750, about 750-800, about 800-850, about 850-900, about 900-950, or about 950-1000 Hz. In some embodiments, the method additionally comprises positioning a magnet on or near a bridge of the subject's nose.

In some embodiments, the biological material comprises cerebrospinal fluid, one or more microbes of the patient's microbiome, one or more components of the patient's metabolome, one or more pathogens, and/or one or more biomarkers of interest. In some embodiments, the biological material comprises amyloid-β, a tau protein, or a combination thereof.

In some embodiments, the magnetic formulation is delivered via a delivery device comprising a cannula and/or microfluidic channel, wherein the cannula and/or microfluidic channel is configured for insertion into a nasal cavity of the subject. In some embodiments, the formulation is delivered via a device comprising: a housing defining first and second insertable portions, each for insertion into a nasal channel of the subject, wherein, upon insertion of the first insertable portion into the nasal channel of the subject, at least one insertable portion engages tissue within the nasal channel to open or expand an internal nasal valve of the subject thereby positioning at least one of the insertable portions for delivery of the formulation to the olfactory region of the subject; and an actuator which delivers the formulation from the either or both of the insertable portions when the device is actuated.

In some embodiments, a method of making a diagnosis of a subject, comprises (a) performing a method described herein, thereby collecting the biological material from the subject; (b) analyzing the collected biological material; and (c) based on the analysis of step b., making the diagnosis. In some embodiments, the method is used for diagnosis of Alzheimer's disease or another neurodegenerative disease. In some embodiments, analyzing the biological material comprises identifying and/or quantifying biomarkers, pathogens, and/or microbes in the collected biological material. In some embodiments, the method further comprises correlating the identified and/or quantified biomarkers, pathogens, and/or microbes with a corresponding physiological characteristic and/or medical condition. In some embodiments, analyzing the biological material comprises using a point-of-care assay system. In some embodiments, the point-of-care assay system is configured to receive a sample of the collected biological material from a delivery device.

In some embodiments, a method of intranasal delivery of a therapeutic agent, comprises delivering a magnetic formulation to an intranasal region of a subject and exposing the subject to a magnetic field. In some embodiments, the magnetic formulation comprises a plurality of magnetic particles and a therapeutic agent. In some embodiments, the magnetic field causes movement of the magnetic particles, thereby enhancing delivery of the therapeutic agent. In some embodiments, the magnetic formulation comprises a fluid suspension. A plurality of solid magnetic particles may be suspended in a fluid or fluid mixture to yield a formulation which behaves like a liquid and can be dispensed as a laminar jet.

In some embodiments, a method of enhancing intranasal contact of a formulation comprises: delivering a magnetic formulation comprising a plurality of magnetic particles to an intranasal region of a subject; and causing oscillation or magnetophoretic movement of at least some of the magnetic particles by exposing the subject to a magnetic field, thereby enhancing intranasal contact of the magnetic formulation. In some embodiments, the magnetic field is an oscillating magnetic field. In some embodiments, the magnetic field is provided via a permanent magnet. In some embodiments, the magnetic field reduces a necessary residence time for the formulation within the nasal cavity.

In some embodiments, a device for intranasal delivery of a magnetic formulation to an olfactory region of a subject and retrieval therefrom comprises: a housing comprising an insertable portion comprising a distal end, a proximal end, and a retrieval magnet; and a subject-engaging portion which engages a columella region of the subject to seat the distal end of the insertable portion within an ejection zone of a nasal channel of the subject; wherein the device is configured to deliver a magnetic formulation to the olfactory region of the subject and to retrieve at least a portion of the magnetic formulation from the olfactory region of the subject. In some embodiments, the device comprises a magnetic portion for retrieval of a portion of the magnetic formulation. In some embodiments, the device dispenses the magnetic formulation as a laminar jet. In some embodiments, the device comprises a compliant dispensing tip comprising a compliant and flexible soft nib. In some embodiments, application of pressure by the subject-engaging portion to the columella region of the subject enables and/or causes delivery of the formulation to the subject from the insertable portion. In some embodiments, the insertable portion comprises a dispensing element for delivery of the magnetic formulation to the olfactory region of the subject.

In some embodiments, a device for intranasal retrieval of magnetic particles comprises: a retrieval magnet; and a magnet support, configured to position the retrieval magnet within a targeted region of a nasal cavity of a subject so as to facilitate retrieval of a plurality of magnetic particles from the targeted region.

In some embodiments, a system for enhancing intranasal contact of a formulation comprises: a device for intranasal delivery of a magnetic formulation comprising a plurality of magnetic particles; and a magnet for causing intranasal movement of the magnetic formulation, thereby enhancing intranasal contact. In some embodiments, the system additionally comprises a support configured to hold the magnet at a desired position on or near a bridge of a subject's nose. In some embodiments, the system additionally comprises a retrieval magnet configured to be inserted within a nasal cavity of a subject for retrieval of a portion of the magnetic formulation. In some embodiments, the retrieval magnet has a diameter of about 2.5 mm. In some embodiments, the system additionally comprises a retrieval magnet configured to be positioned outside a nasal cavity of a subject for retrieval of a portion of the magnetic formulation.

In some embodiments, a magnetic formulation for intranasal biomarker sampling comprises a plurality of magnetic particles configured to capture biological material once delivered within the nasal cavity, wherein the delivered formulation is configured to be withdrawn from the nasal cavity with the biological material. In some embodiments, the magnetic particles are coated with tau antibodies, beta-amyloid antibodies, or a combination thereof. In some embodiments, the magnetic particles comprise a first plurality of magnetic particles, coated with tau antibodies, and a second plurality of magnetic particles, coated with beta-amyloid antibodies. In some embodiments, the magnetic particles have an average diameter of about 50 micrometers.

In some embodiments, the magnetic particles have an average diameter of about 0.01-0.015, about 0.015-0.02, about 0.02-0.025, about 0.025-0.03, about 0.03-0.035, about 0.035-0.04, about 0.04-0.045, about 0.045-0.05, about 0.05-0.055, about 0.055-0.06, about 0.06-0.065, about 0.065-0.07, about 0.07-0.075, about 0.075-0.08, about 0.08-0.085, about 0.085-0.09, about 0.09-0.095, about 0.095-0.1, about 0.1-0.15, about 0.15-0.2, about 0.2-0.25, about 0.25-0.3, about 0.3-0.35, about 0.35-0.4, about 0.4-0.45, about 0.45-0.5, about 0.5-0.55, about 0.55-0.6, about 0.6-0.65, about 0.65-0.7, about 0.7-0.75, about 0.75-0.8, about 0.8-0.85, about 0.85-0.9, about 0.9-0.95, about 0.95-1, about 1-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, about 95-100, about 100-105, about 105-110, about 110-

115, about 115-120, about 120-125, about 125-130, about 130-135, about 135-140, about 140-145, about 145-150, about 150-155, about 155-160, about 160-165, about 165-170, about 170-175, about 175-180, about 180-185, about 185-190, about 190-195, about 195-200, about 200-210, about 210-220, about 220-230, about 230-240, about 240-250, about 250-260, about 260-270, about 270-280, about 280-290, about 290-300, about 300-320, about 320-340, about 340-360, about 360-380, about 380-400, about 400-420, about 420-440, about 440-460, about 460-480, or about 480-500 micrometers.

In some embodiments, the formulation is delivered to the olfactory region of the nasal cavity. In some embodiments, the formulation is configured to capture biological material from a targeted sub-region of the nasal cavity. In some embodiments, the delivered formulation is configured to preserve the captured biological material when being withdrawn. In some embodiments, the biological material comprises cerebrospinal fluid (CSF), one or more microbes of the patient's microbiome, one or more components of the patient's metabolome, one or more pathogens, and/or one or more biomarkers of interest. In some embodiments, the formulation is configured to capture specific biological material.

In some embodiments, the formulation comprises a buffered saline solution, a polyethylene glycol, a glycerol, or a combination thereof. In some embodiments, the buffered saline solution is 100 mM phosphate buffered saline. In some embodiments, the formulation comprises one or more gelling agents and/or thickeners. In some embodiments, the formulation comprises a viscosity between about 20-40 cP. In some embodiments, the formulation comprises a viscosity between about 0-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, or about 95-100 cP. In some embodiments, the formulation comprises a viscosity between about 100-110, about 110-125, about 125-150, about 150-200, about 200-250, about 250-300, about 300-350, about 350-400, about 400-450, about 450-500, about 500-550, about 550-600, about 600-650, about 650-700, about 700-750, about 750-800, about 800-850, about 850-900, about 900-950, or about 950-1000 cP. In some embodiments, the formulation comprises a viscosity modifier to provide a desired viscosity for the formulation. In some embodiments, the viscosity modifier comprises at least one of glycerol, pectin, and polyethylene glycol. In some embodiments, the viscosity modifier comprises 25-75% of the formulation by volume.

In some embodiments, the formulation is configured for removal from the nasal cavity using a magnet. In some embodiments, the formulation comprises one or more specific mono or polyclonal antibodies so as to target a specific biological material. In some embodiments, the formulation comprises one or more specific aptamers so as to target a specific biological material. In some embodiments, the formulation is provided, delivered, and/or withdrawn as a bolus of the formulation.

In some embodiments, a magnetic formulation for intranasal delivery of a therapeutic agent comprises a magnetic formulation comprising a plurality of magnetic particles and a therapeutic agent, wherein the magnetic particles are configured to enhance intranasal contact of the therapeutic agent. In some embodiments, the formulation is delivered to the olfactory region of the nasal cavity.

Example Apparatus and Methods

As described in more detail below, FIGS. 2A-2F, FIGS. 3A-3D, and FIGS. 4A-4F illustrate exemplary embodiments for collecting biological material from a target region of the nasal cavity of a patient, such as the olfactory region of the nasal cavity. The exemplary embodiments and methods as described herein are also applicable to collecting biological material from other regions of the nasal cavity, as disclosed herein. FIGS. 2A-2F show steps of an exemplary method using a device 200 comprising a common cannula 202 and separate containers 220 and 250 for delivering and recovering the formulation respectively. FIGS. 3A-3D show steps of an exemplary method using a device 300 comprising a cannula 302 and an attached bulb 304 for both delivering and recovering the formulation. FIGS. 4A-4F shows steps of an exemplary method using a device 400 comprising a container 420 with a cannula 402 for formulation delivery, and another container 450 with a cannula 452 for formulation recovery. Details of these example devices and their operation are described below.

Figure 2A:
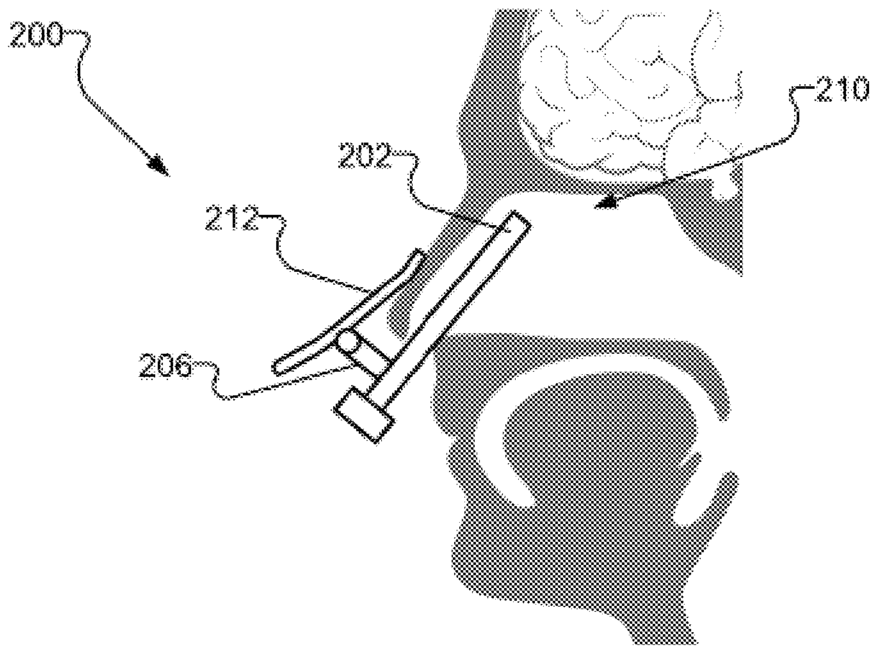
FIG. 2A depicts an illustration of an embodiment for collecting biological material from a nasal cavity, wherein the embodiment comprises a device comprising a cannula that is inserted into the nasal cavity.
Figure 2B:
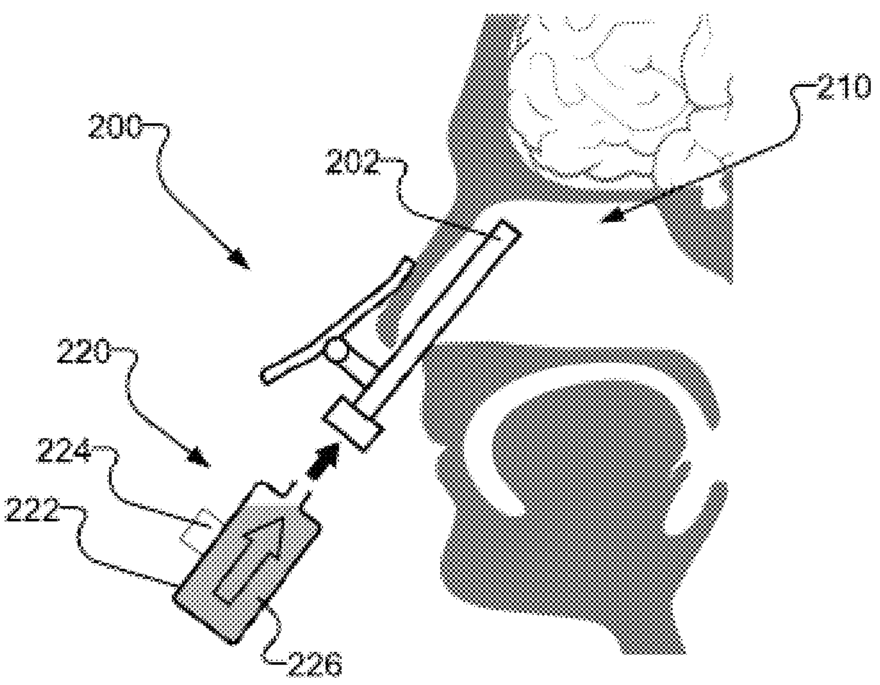
FIG. 2B depicts an illustration of the embodiment for collecting biological material according to FIG. 2A, wherein a container holding formulation is coupled to the cannula.

As shown in FIG. 2A, the device 200 comprises a flexible, rigid, or conforming cannula 202. In some embodiments, the cannula at 202 incorporates a sheathing mechanism to protect the olfactory region from contamination from the lower nasal cavity and protect the biological material from contamination during the acquisition phase. In some embodiments, the device 200 comprises a container 220 (FIG. 2B) with a body for holding the formulation 226. In some embodiments, the container 220 comprises a deployment mechanism 224 for ejecting the formulation 226 from the container 220 as shown in FIG. 2B. In some embodiments, the container 220 is removably attached to the cannula 202. In some embodiments, the container 220 comprises a carpule 222.

In some embodiments, the device 200 is located against the external base of the nose. For example, in some embodiments, as shown in FIG. 2A, the device comprises a clip 212 mounted on a clip base 206. The clip 212 provides an anatomical reference point for accurate placement of the cannula 202 and maintains consistent placement of the cannula 202.

In some embodiments, the cannula 202 is a fixed length suited for the general population. In some embodiments, the cannula 202 is of a variable length that is set to a patient's specific measurements. For example, in some embodiments, the cannula 202 is slidably attached to the base 206 such that it may be moved relative to the clip 212. In some embodiments, the cannula 202 includes graduations (e.g. markings on the cannula) to assist placement. The graduations may be used to insert the cannula to a pre-determined depth, for example, such that the tip of the cannula 202 reaches the olfactory region 210 but does not damage the tissue. In some embodiments, the pre-determined depth is, for example, determined by taking a pre-insertion measurement with a CT scan or otoscope for an individual patient or by utilizing a maximum safe length as determined by analyzing a database of pool anthropometric measurements of the nasal cavity.

Figure 2C:
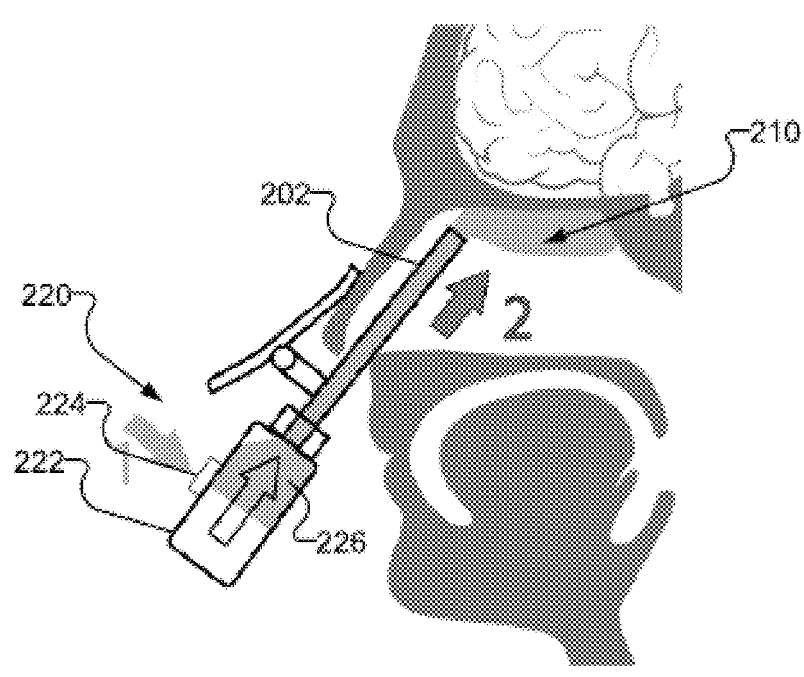
FIG. 2C depicts an illustration of the embodiment for collecting biological material according to FIG. 2A, wherein the formulation is delivered to the nasal cavity.

In some embodiments, the deployment mechanism comprises any delivery mechanism as disclosed herein. For example, as shown in FIG. 2B, the deployment mechanism 224 is coupled to the container 220, and is configured such that when the deployment mechanism 224 is activated, the formulation 226 is ejected from the container 220, through the cannula 202 and is deposited in the olfactory region 210 of the patient, as shown in FIG. 2C. In some embodiments, the deployment mechanism is activated by a user. In some embodiments, the cannula 202 comprises an orifice that is positioned to deliver the formulation 226 to a targeted sub-region (not shown).

In some embodiments, the deployment mechanism 224 comprises a button, a spring, and a plunger (not shown). When the button is pressed, this releases the spring, which moves the plunger to force the formulation 226 from the container 220 into the olfactory region 210. The deployment mechanism 224 may take other forms in other embodiments.

Figure 2D:
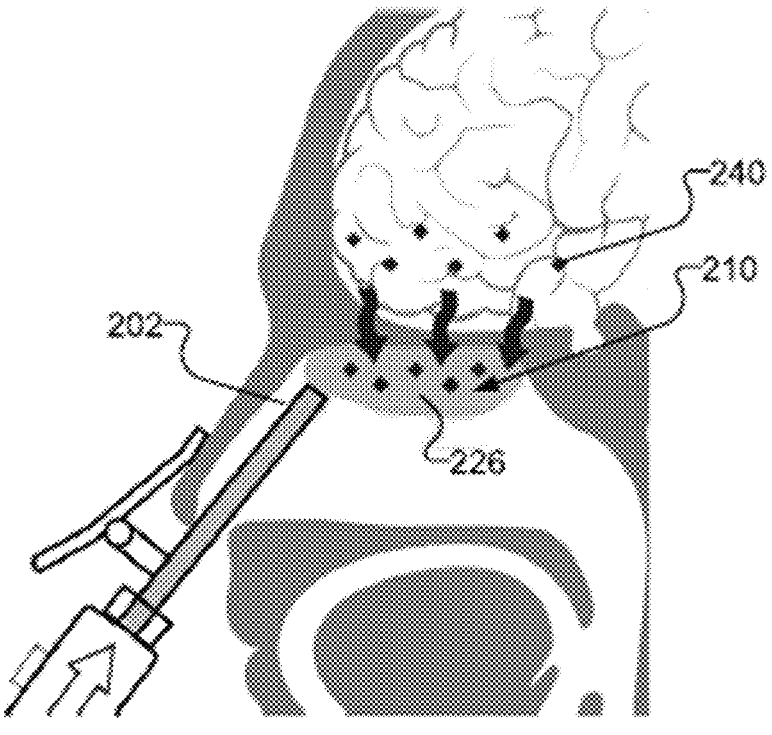
FIG. 2D depicts an illustration of the embodiment for collecting biological material according to FIG. 2A, wherein biological material is captured by the formulation.

As described above, in some embodiments the formulation has a higher osmolality than the mucus in the olfactory region 210. In some embodiments, the formulation includes sugars to both increase osmolality and to create a cohesive fluid body that can be fully extracted. In some embodiments, the increased osmolality creates an osmotic pressure gradient that favors uptake of the biological material, such as a specific biomarker target 240, into the formulation 226 deposited in the olfactory region 210, as shown in FIG. 2D. In some embodiments the formulation 226 is shear thinning to promote distribution of the formulation 226 into the narrow spaces within the olfactory region 210.

Figure 2E:
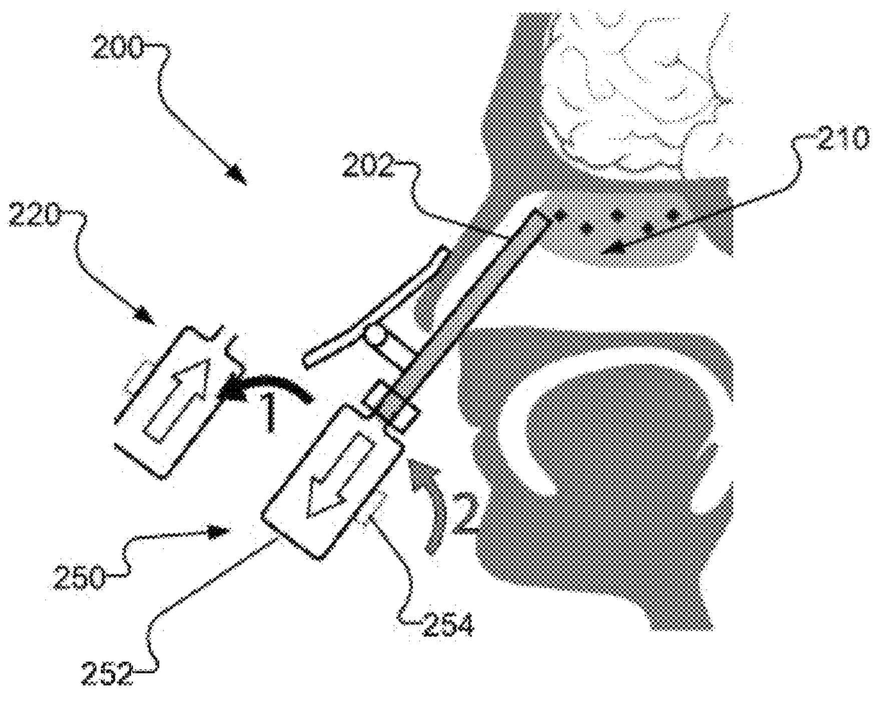
FIG. 2E depicts an illustration of the embodiment for collecting biological material according to FIG. 2A, wherein a recovery vessel is coupled to the cannula to withdraw and collect the biological material.
Figure 2F:
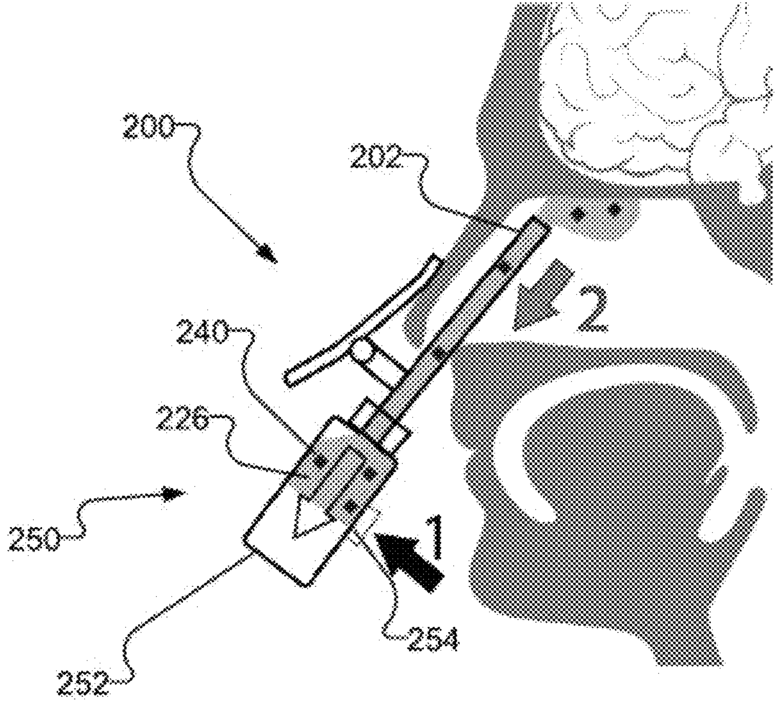
FIG. 2F depicts an illustration of the embodiment for collecting biological material according to FIG. 2A, wherein the formulation and captured biological material is withdrawn through the cannula and into the recovery vessel.

In some embodiments, recovery of the formulation and/or biological material comprises any recovery mechanism as disclosed herein. For example, as shown in FIG. 2E, in some embodiments, the container 220 is disconnected from the cannula 202 and replaced with a recovery vessel 250. In some embodiments, the recovery vessel 250 comprises a body configured to hold the withdrawn formulation and/or biological material. In some embodiments, the recovery vessel 250 comprises a carpule 252, a deployment button 254, a spring (not shown) and/or a plunger (not shown). As shown in FIG. 2F, when the deployment button 254 is pressed, the spring moves the plunger which draws the formulation 226 and biological material 240 through the cannula 202 into the recovery vessel 250. In some embodiments, system geometry and rate of travel of the plunger are controlled (e.g. by damping) to ensure the formulation 226 is not drawn in too quickly (e.g. minimize or prevent shear forces experienced by the captured biological material 240 from affecting analysis results through damage to the contents of the captured biological material, and minimizing or preventing air from being recovered instead of the full amount of formulation and biological material).

The formulation 226 is any formulation as disclosed herein. For example, in some embodiments, the formulation shown in FIG. 2F is crosslinked upon exposure to air or other means (as described herein), thereby changing the formulation into a semi-solid state. In some embodiments, the semi-solid formulation facilitates preservation of the captured biological material according to its target site localization while the semi-solid formulation is withdrawn and preserved in the vessel 252.

In some embodiments, the cannula 202 is sheathed to prevent or minimize cross contamination of the biological material and/or contamination of the olfactory region through cannula inoculation from the lower nasal anatomy.

Figure 3A:
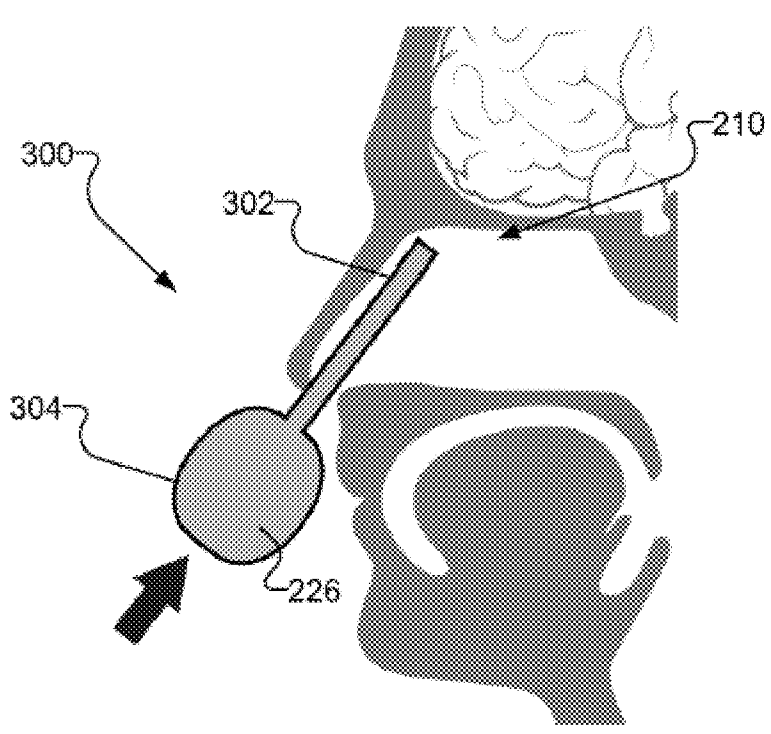
FIG. 3A depicts an illustration of another embodiment for collecting biological material from a nasal cavity, wherein the embodiment comprises a device comprising a flexible bulb, and a cannula that is inserted into the nasal cavity.
Figure 3B:
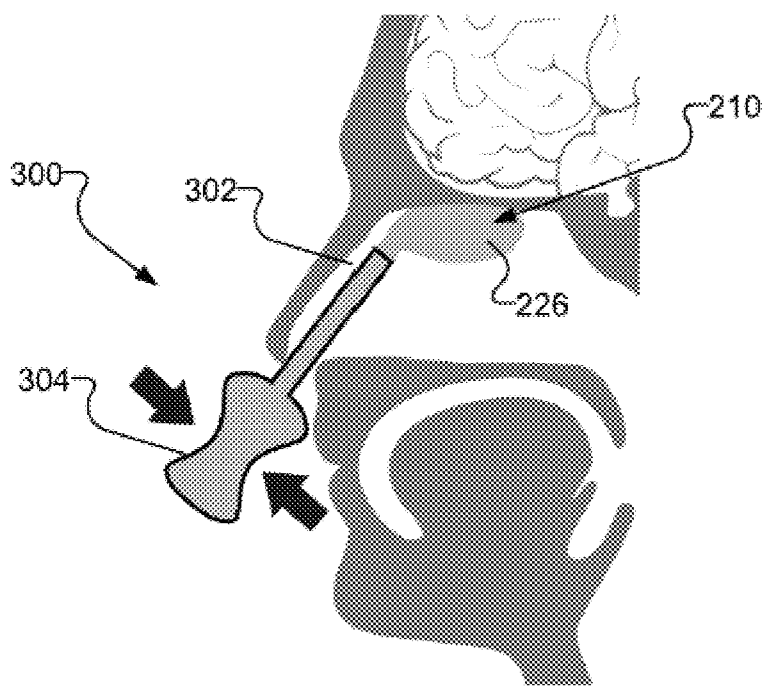
FIG. 3B depicts an illustration of the embodiment for collecting biological material according to FIG. 3A, wherein the formulation is delivered to the nasal cavity by pressing on the flexible bulb.

FIG. 3A shows another embodiment of a device 300 comprising a cannula 302 and a flexible bulb 304. As shown in FIG. 3B, pressing on the flexible bulb 304 pushes the formulation 226 through the cannula 302 and into the olfactory region 210. In some embodiments, the cannula 302 comprises an orifice that is positioned to deliver the formulation 226 to a targeted sub-region (not shown). The formulation is any formulation as disclosed herein.

Figure 3C:
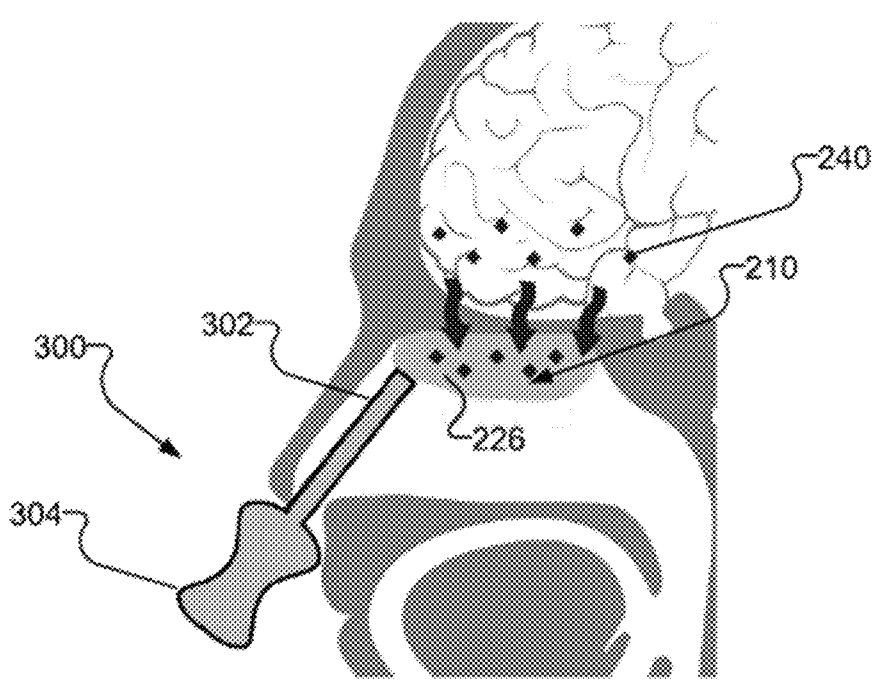
FIG. 3C depicts an illustration of the embodiment for collecting biological material according to FIG. 3A, wherein biological material is captured by the formulation.

FIG. 3C shows a formulation 226 with a higher osmolality than the biological material 240, creating an osmotic pressure gradient that favors uptake of the biological material, including biomarkers of interest contained therein 240, into the formulation 226.

Figure 3D:
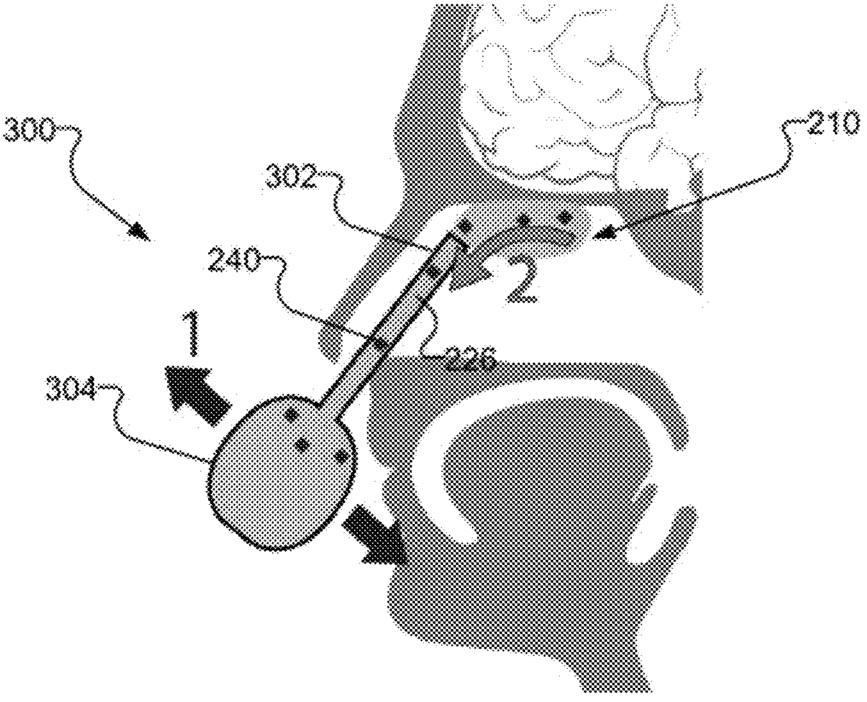
FIG. 3D depicts an illustration of the embodiment for collecting biological material according to FIG. 3A, wherein the flexible bulb is allowed to relax to withdraw and capture the biological material.

As shown in FIG. 3D, the flexible bulb 302 is allowed to relax, drawing the formulation 226 and biological material 240 through the cannula 302 back into the bulb 304.

In some embodiments, the cannula 302 is sheathed to prevent or minimize cross contamination of the biological material and/or contamination of the olfactory region through cannula inoculation from the lower nasal anatomy.

FIGS. 4A-D shows a device 400 comprising a container 420 holding formulation 226 with a deployment mechanism 424 configured to eject the formulation through a cannula 402, similar to the operation of device 200 described above. In some embodiments, the container 420 comprises a carpule 422. In some embodiments, the cannula 402 comprises an orifice that is positioned to deliver the formulation 226 to a targeted sub-region (not shown). In some embodiments, the deployment mechanism comprises any delivery mechanism as disclosed herein. The formulation is any formulation as disclosed herein.

Figure 4A:
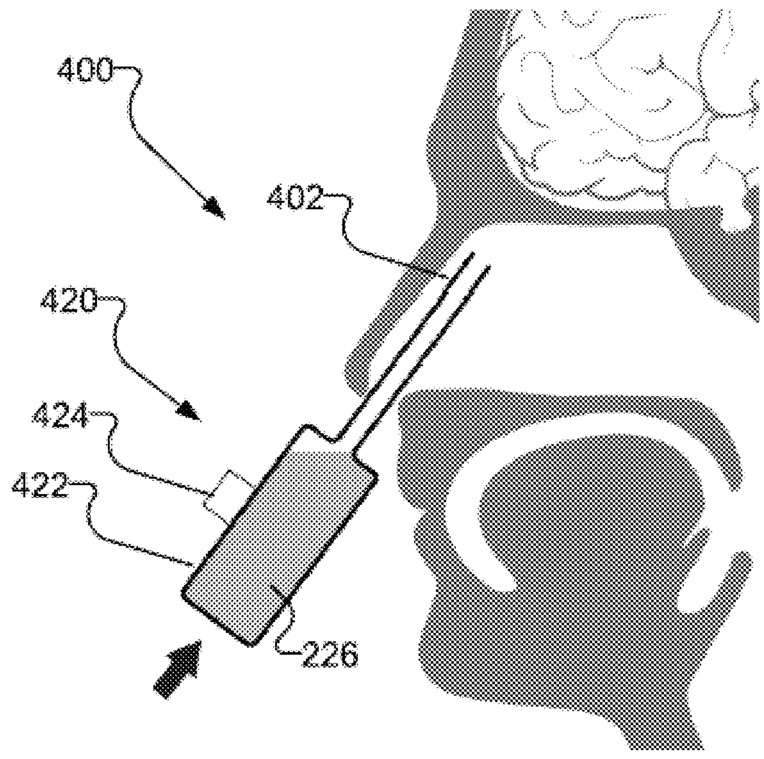
FIG. 4A depicts an illustration of another embodiment for collecting biological material from a nasal cavity, wherein the embodiment comprises a delivery device comprising a container holding the formulation, a deployment mechanism, and a cannula that is inserted into the nasal cavity.
Figure 4B:
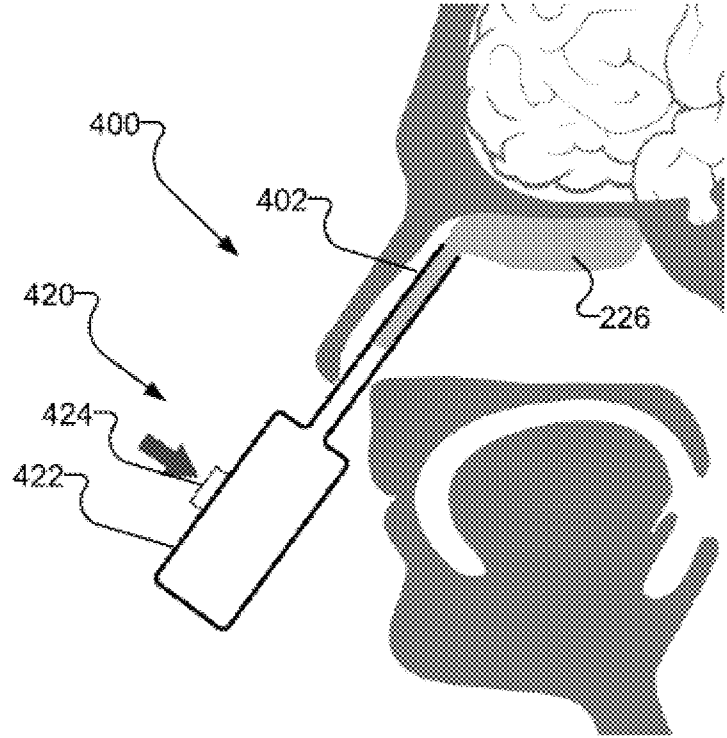
FIG. 4B depicts an illustration of the embodiment for collecting biological material according to FIG. 4A, wherein the formulation is delivered to the nasal cavity by pressing on the deployment mechanism.
Figure 4C:
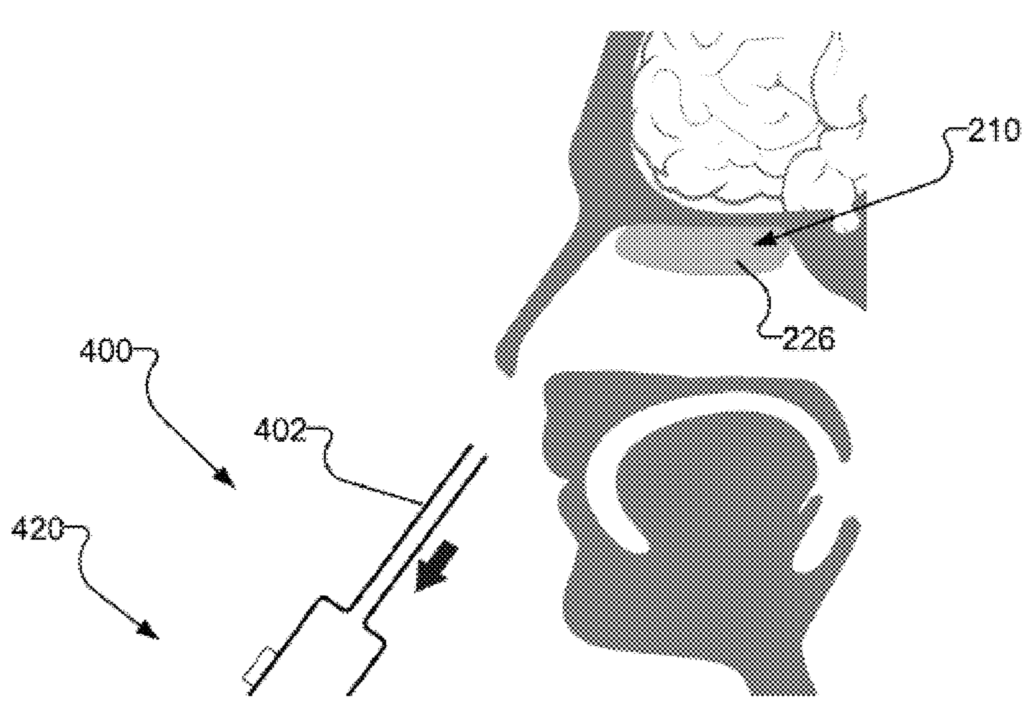
FIG. 4C depicts an illustration of the embodiment for collecting biological material according to FIG. 4A, wherein the delivery device is removed from the nasal cavity.
Figure 4D:
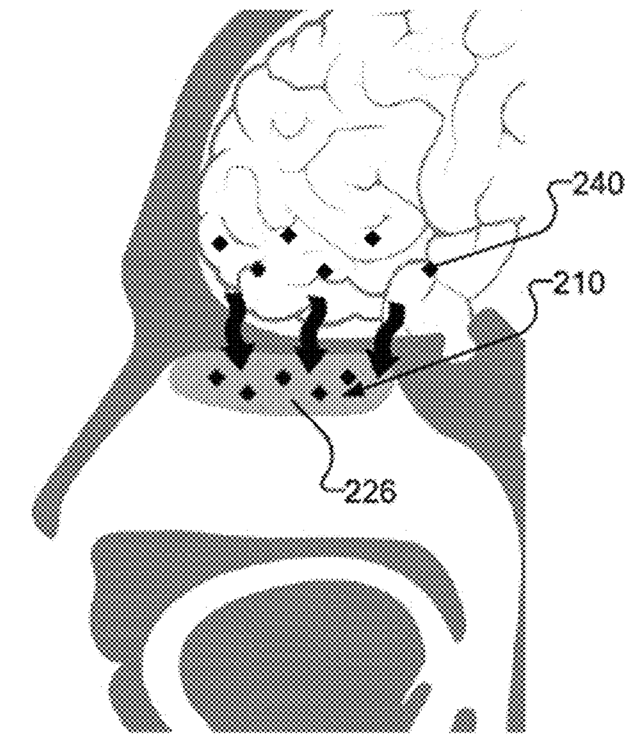
FIG. 4D depicts an illustration of the embodiment for collecting biological material according to FIG. 4A, wherein biological material is captured by the formulation.
Figure 4E:
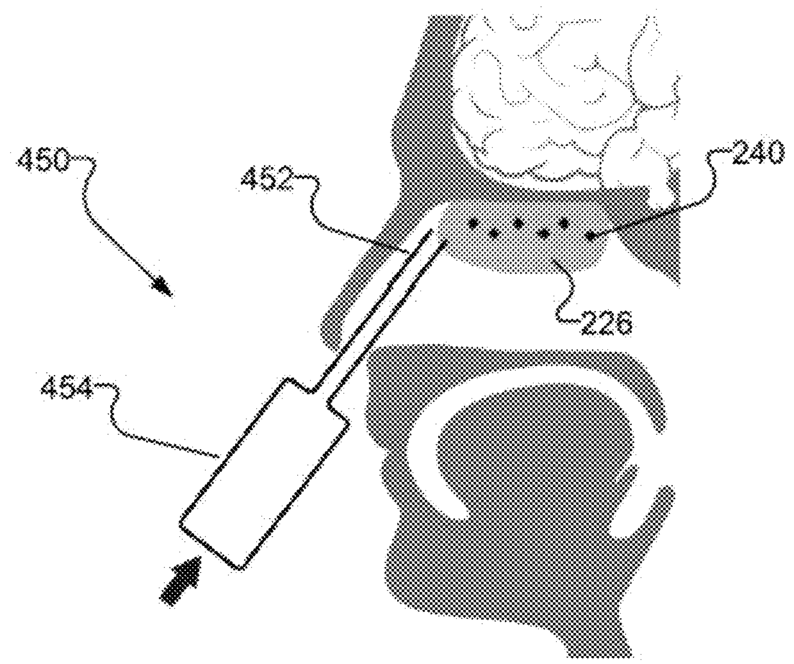
FIG. 4E depicts an illustration of the embodiment for collecting biological material according to FIG. 4A, wherein a recovery device and recovery cannula, filled with wicking material, is inserted into the nasal cavity.
Figure 4F:
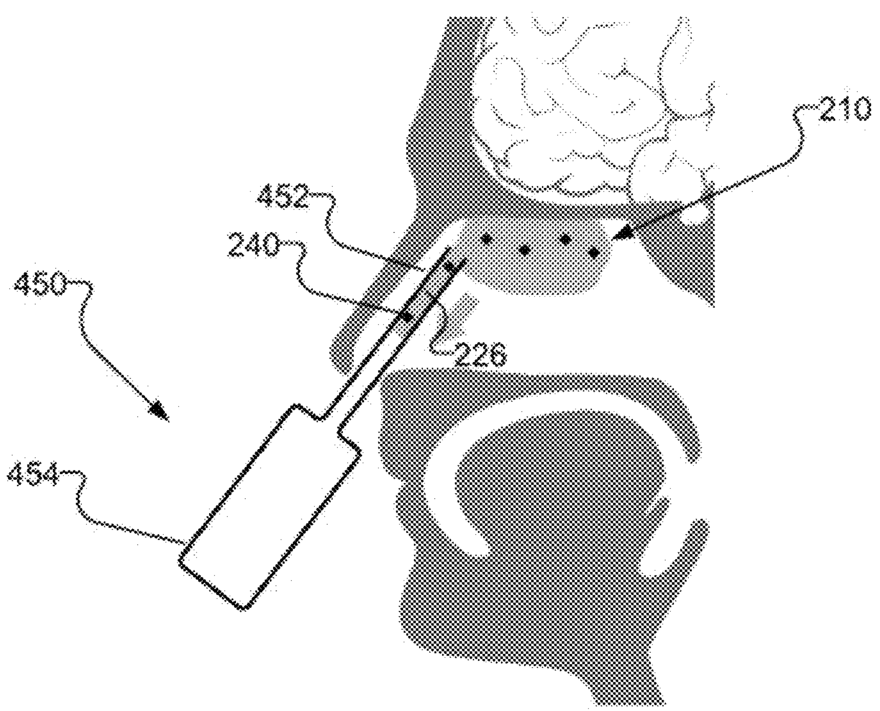
FIG. 4F depicts an illustration of the embodiment for collecting biological material according to FIG. 4A, wherein the recovery device draws the formulation and biological material through the cannula using the wicking material.

As shown in FIG. 4E, a recovery device 450 may be inserted into the patient's nose. In some embodiments, the recovery device comprises a body for holding the formulation and/or biological material after being withdrawn. In some embodiments, the recovery device comprises a recovery cannula different from the cannula used to deliver the formulation to the olfactory region. In some embodiments, the recovery cannula is detachably coupled to a recovery vessel. In some embodiments, the recovery device comprises any recovery mechanism as disclosed herein. For example, in some embodiments, the recovery device has a chamber 454 filled with wicking material and a recovery cannula 452 filled with wicking material configured to wick fluid. In some embodiments, the wicking material comprises natural or synthetic fibers, spun, woven or randomly oriented, and/or capillary tubes that wick fluid. In some embodiments, the recovery device 450 and wicking material is used to draw the formulation 226 and biological material 240 from the patient's olfactory region 210, as shown in FIG. 4F.

In some embodiments, the cannula 402 is sheathed to prevent or minimize cross contamination of the biological material and/or contamination of the olfactory region through cannula inoculation from the lower nasal anatomy.

The foregoing discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Example Use Case Scenario A: In some embodiments, formulations, methods, and devices described herein provide the ability for at-home testing. As a non-limiting example, steps similar to the following steps may be used for at-home testing.

Step 1. A doctor prescribes a biomarker detection kit.

Step 2. A patient obtains a test kit—The patient picks up kit at a pharmacy, receives it in the mail or it is available over the counter at the pharmacy.

Step 3. Opening test kit—The patient opens the test kit with two parts to the contents. Part one: a precision Olfactory Delivery Device that contains the formulation including coated magnetic beads that will collect the specific biomarkers of interest. Part two: a magnetic tipped nasal inserter and a magnetic collection vessel with dilution fluid connected to a lateral flow assay that has the capability of communicating a positive or negative result, namely in relation to evidence of the biomarker of interest.

Step 4. Delivery of formulation with selectively binding beads—The patient delivers fluid to olfactory region and waits for a predetermined number of minutes.

Step 5. Retrieval of fluid with bound biomarkers-After the predetermined number of minutes has elapsed, the patient puts the collection container to their nose and tilts their head downward. The magnetic ends of the collection container draw out the formulation into the collection container.

Step 6. The sample is analyzed via contact with a lateral flow assay.

Step 7. The result of the analysis is read by the patient.

Example Use Case Scenario B: In some embodiments, formulations, methods, and devices described herein provide the ability for in-clinic testing. As a non-limiting example, steps similar to the following steps may be used for in-clinic testing.

Step 1. A doctor prescribes a test which has been linked to a particular disease or ailment via clinical trials.

Step 2. The patient goes to the test facility, possibly after some liquid intake requirements.

Step 3. The patient is seated, optionally fixed in place, and possibly inverted with respect to gravity.

Step 4. The technician retrieves the magnetic liquid swab containing a number of magnetic beads from a special storage (e.g. a cooler maintaining a specified low temperature).

Step 4*. (Possible alternative to Step 4) The magnetic beads are coated on-site to avoid potential degradation.

Step 5. The technician loads the device in a clean space (Note that a pre-loaded device could be used as an alternative).

Step 6. The technician conducts a pre-administration routine with the patient, and clips an external electromagnet to their nose.

Step 7. The technician inserts the device into the patient's nose and ejects the sample Step 8. The nose-clip generates an oscillatory magnetic field targeting the olfactory cleft (OC) to enhance mixing and steer magnetic beads to the target site.

Step 9. The ejection device is removed from the nose.

Step 10. After a predetermined period of time, the beads are retrieved by lavage, by a magnetic tip on an inserter, by blowing the nose into a special tissue, or by another suitable sample removal method or device.

Step 11. The sample is taken to a cleaning station, rinsed, and packaged.

Step 12. The cleaned sample is labelled and placed into the queue for analysis.

Step 13. The sample is fed into an ELISA machine and analyzed.

Step 14. The results are processed and tabulated to show which biomarkers are identified as present and quantities and ratios of identified biomarkers.

Step 15. Results are shared with doctors for assessment and possible diagnosis.

Example 1: Methods for Analysis of Magnetic Beads with Attached Proteins Captured from the Olfactory Cleft A first example method involves steps to elute and assay (measure) isolated protein by a simple assay such as an ELISA kit, by a lateral flow assay, or by another immunoassay. A second example method involves steps to assay the protein-bead complex. Exemplary magnetic beads include MagSi-DNA 3.0 μm silica-coated superparamagnetic beads (Magtivia part #MDOX022, purchased from Boca Scientific Inc, Dedham, MA), Dynabeads Protein G Immunoprecipitation Kit (Invitrogen part #10007D), optionally coated with AB42 antibodies (Anti-β-Amyloid Antibody, Mouse monoclonal (Sigma part #A3981)), and superparamagnetic iron oxide nanoparticles (e.g. SPIONS, 80 nm). Lateral flow immunoassays (pregnancy type strip tests) use beads as carriers for antibodies and proteins. The elation step of the first example may be eliminated, and the beads may be added in some standard (buffer) solution to a lateral flow assay. An example sample pad may have two separate strips, one for beta amyloid 42 ("AB42") and one for t-tau. Taking the AB42 strip as an example, a 'test' line would have anti-AB42 antibodies on it which would bind AB42 protein picked up by the beads. Beads that did pick up AB42 would get stuck at the test line. Downstream would be a 'control' line with AB42 protein (or another antibody binder) to bind the remaining beads.

Similar mechanics on the t-tau strip would result in a protein ratio. Measurement may be accomplished colorimetrically, (ie with a camera), but that doesn't take into account the vast majority of beads that lie below the surface of the test strips. Here, given the magnetic properties of the beads, another option would be to use a magnetic lateral flow analyzer instrument, which would pick up signal from all beads through the thickness of the lateral flow membrane, thereby substantially enhancing signal and enabling higher analytical precision. A magnetic reader for lateral flow assays may allow for fully quantitative assays, instead of semi-quantitative, all at low cost and simple to operate.

On-bead analysis may be accomplished via ELISA. After protein collection in vivo with antibody-coated beads, a detection antibody may be added. The detection antibody could simply have a tag (e.g. fluorescent or chemiluminescent) that could be detected directly with an imaging device, or could be detected indirectly. With indirect detection, one option could be to bind the detection antibody to horseradish peroxidase (HRP) enzyme. This reacts with a liquid 'substrate,' which in the case of HRP can be tetramethylbenzidine (TMB). HRP turns TMB blue. The more protein collected, the greater the color intensity. The reaction may be quenched via the addition of an acid, and absorbance of 450 nm light (blue) may be measured via an instrument to provide quantitative data.

Tau Protein: Tau is a protein that helps stabilize the internal skeleton of nerve cells (neurons) in the brain. This internal skeleton has a tube-like shape through which nutrients and other essential substances travel to reach different parts of the neuron. In Alzheimer's disease (AD), an abnormal form of tau builds up and causes the internal skeleton to fall apart. These abnormal forms of tau protein cling to other tau proteins inside the neuron and form tau tangles. Tau tangles and amyloid-beta plaques—large accumulations of microscopic brain protein fragments that slow a person's ability to think and remember—are hallmarks of Alzheimer's disease. Total tau, or t-tau is one option for measurement. Some portion of the total tau may be phosphorylated tau.

Amyloid-beta 42 Protein (AB42): The beta-amyloid (or amyloid-beta) protein fragment involved in Alzheimer's comes in several different molecular forms that collect between neurons. It is formed from the breakdown of a larger protein, called amyloid precursor protein. One form, beta-amyloid 42 is thought to be especially toxic. In the Alzheimer's brain, abnormal levels of beta-amyloid 42 clump together to form plaques that collect between neurons and disrupt cell function.

The Tau: AB42 Ratio as a Diagnostic Indicator of Alzheimer's: While the individual concentrations of various CSF proteins have been used to help diagnose AD, the ratios between various concentrations have now been shown to better distinguish AD patients from other patients. One of the promising ratios is the Tau: AB42 ratio.

The following represent possible threshold values for physiological concentrations indicative of healthy patients:

| | |
|---|---|
| Tau <300 pg/mL | 21-50 years old |
| Tau <450 pg/mL | 51-70 years old |
| Tau <550 pg/mL | 71-93 years old |
| AB42 >500 pg/mL | for all ages |

Example Diagnostic Biomarkers and their Antibodies

| Item | Name | Manufacturer/Vendor | Part Number |
|---|---|---|---|
| TAU protein | tau-441 (1-421) recombinant protein | Sigma-Aldrich | SRP0701 |
| TAU antibody | tau monoclonal antibody (T46) * | Invitrogen | 136400 |
| TAU antibody | tau monoclonal antibody (Tau-5) | Invitrogen | AHB0042 |
| TAU antibody | recombinant anti-tau antibody EPR22524-95 | Abcam | AB254256 |
| TAU antibody | recombinant anti-tau (MBD region) antibody EPR25205-233 | Abcam | AB308439 |

Tau protein naturally exists in 6 different forms, ranging in length from 352-441 amino acids. The longest form is called tau-441. This form of tau has been known to be truncated by proteases (enzymes) just after the 421st amino acid. This truncated form of tau-441 has been implicated in Alzheimer's Disease. The tau-441 (1-421) of this example is that truncated version of tau-441.

Example 2: Liquid Swab Formulation

Magnetic Beads in Liquid Swabs: Examples, including measurement of diagnostic biomarkers, used magnetic beads coated with antibodies to capture biomarkers in CSF. To evaluate the influence of viscosity on the ease with which the beads can be moved with a magnetic field, the manipulation of magnetic beads in liquid swab formulations was tested.

Magnetic Beads: The magnetic beads used in examples including measurement of diagnostic biomarkers measured 2.8 μm in diameter. Beads measuring 50 μm in diameter were used for the manipulation of beads in liquid swabs. This is on the upper end of typical bead size and maximizes the force developed on the bead by the magnetic field because: force exerted on bead by magnetic field varies as diameter to the third power. For perspective, the force exerted by the same magnetic field on 50 μm beads is 5,694 times larger than on 2.8 μm beads.

Liquid Swabs: The liquid swabs used were 1 cP plain water and 39 cP PEG hydrogel.

Figure 5:
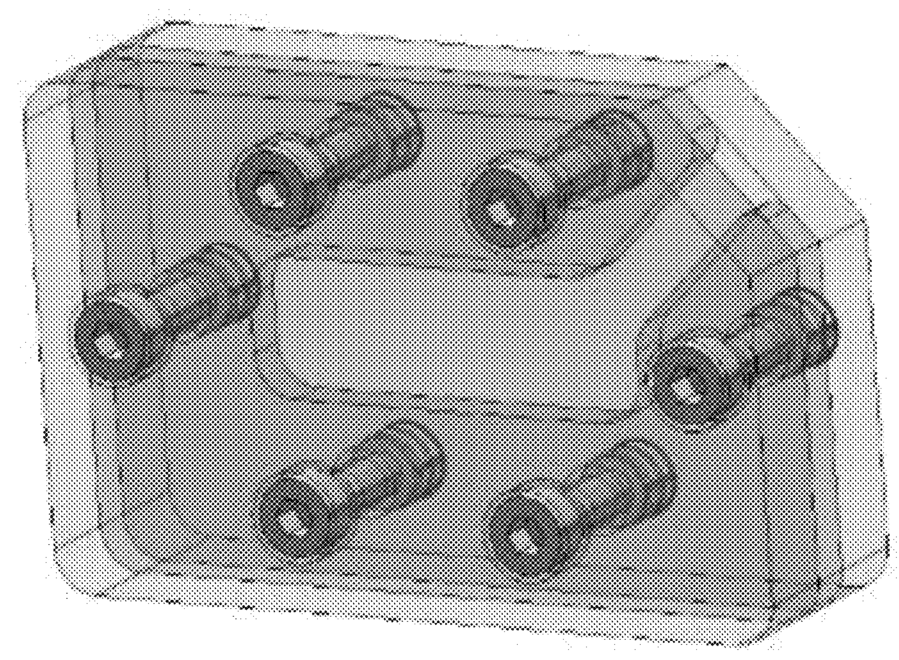
FIG. 5 depicts a simplified nasal model constructed from three machined polycarbonate plates.

Nasal Cavity Model: FIG. 5 shows a simplified nasal cavity constructed from 3 machined polycarbonate plates. These plates are extremely transparent and result in a nasal model that is much more transparent than 3D printed nasal models. The olfactory cleft inside the model measured 10 mm high×30 mm wide×3 mm thick.

Magnet: The magnet used (McMaster-Carr part number 5848K46) was rated for a maximum pull of 94 lb (based on direct contact with a rust-free, unpainted iron plate).

Bead Motion with Different Liquid Swab Viscosities: Increasing the swab viscosity from 1 cP (water) to 39 cP (PEG) had a profound effect on the speed with which the 50 μm beads moved through the swab.

Example 2.1: The beads were pulled from the bottom to the top of the olfactory cleft by placing the magnet on top of the nasal model. The time required for the beads to reach the top of the olfactory cleft slowed from 1 second in 1 cP water to 20+ seconds in the 39 cP PEG.

Figure 6:
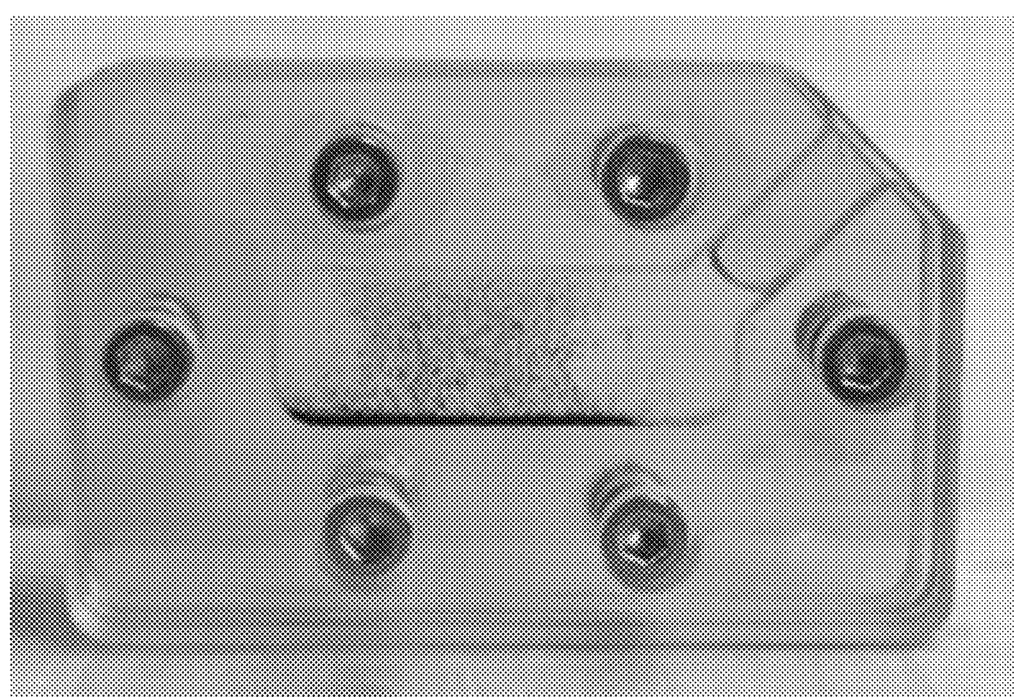
FIG. 6 depicts beads settling in water (1 cP) after a few seconds within the nasal model. The diagonal channel of the nasal model corresponds to a human nasal passage. Because the nasal model is oriented upside down in relation to a human nasal cavity, the flat bottom surface of the cavity within the nasal model corresponds to the olfactory region.
Figure 7:
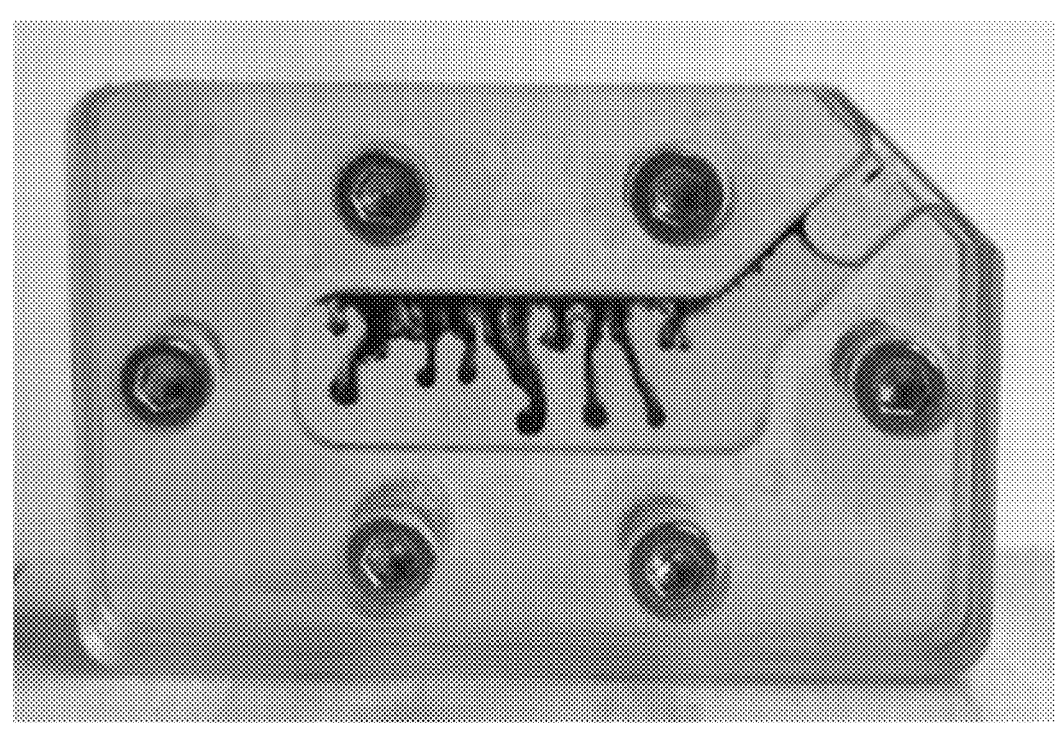
FIG. 7 depicts beads settling in water (39 cP) after 30 seconds within the nasal model.

Example 2.2: The beads were allowed to passively settle back down to the bottom of the olfactory cleft by removing the magnet from the top of the nasal model. The time required for the beads to reach the bottom of the olfactory cleft slowed from just a few seconds in water to 60+ seconds in the PEG. See FIG. 6 and FIG. 7.

Bead Retrieval using Small Magnets in Nasal Passage: The nasal model was used with a swab viscosity of 1 cP (water) to look at 50 μm bead retrieval using small magnets inserted into the nasal passage.

The small magnets used were McMaster-Carr part number 5862K426. These are cylindrical magnets rated at a maximum pull of 0.4 lbs. This is quite a weak pull but the magnet was chosen for its 2.5 mm diameter, which just fits inside the 3 mm thick nasal passage and olfactory cleft of the nasal model. A stack of 14 magnets was used to reach deeply into the model.

Figure 8:
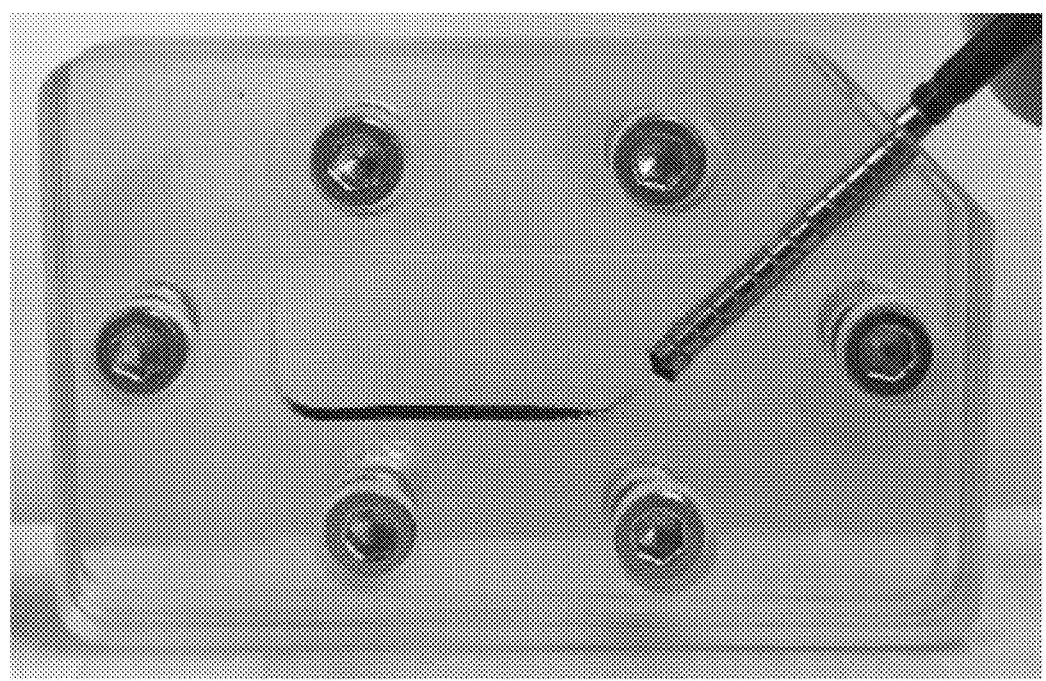
FIG. 8 depicts bead retrieval using small magnets within the model nasal passage.

The initial intent was to keep the magnets out of the olfactory cleft area of the model, but the magnets were too weak to retrieve the beads at any distance longer than ~5 mm. Accordingly, magnets were inserted into the olfactory cleft in order to retrieve any beads, as shown in FIG. 8. This is sub-optimal, as hard objects inserted into the olfactory cleft may damage the fragile cribriform plate.

Figure 9:
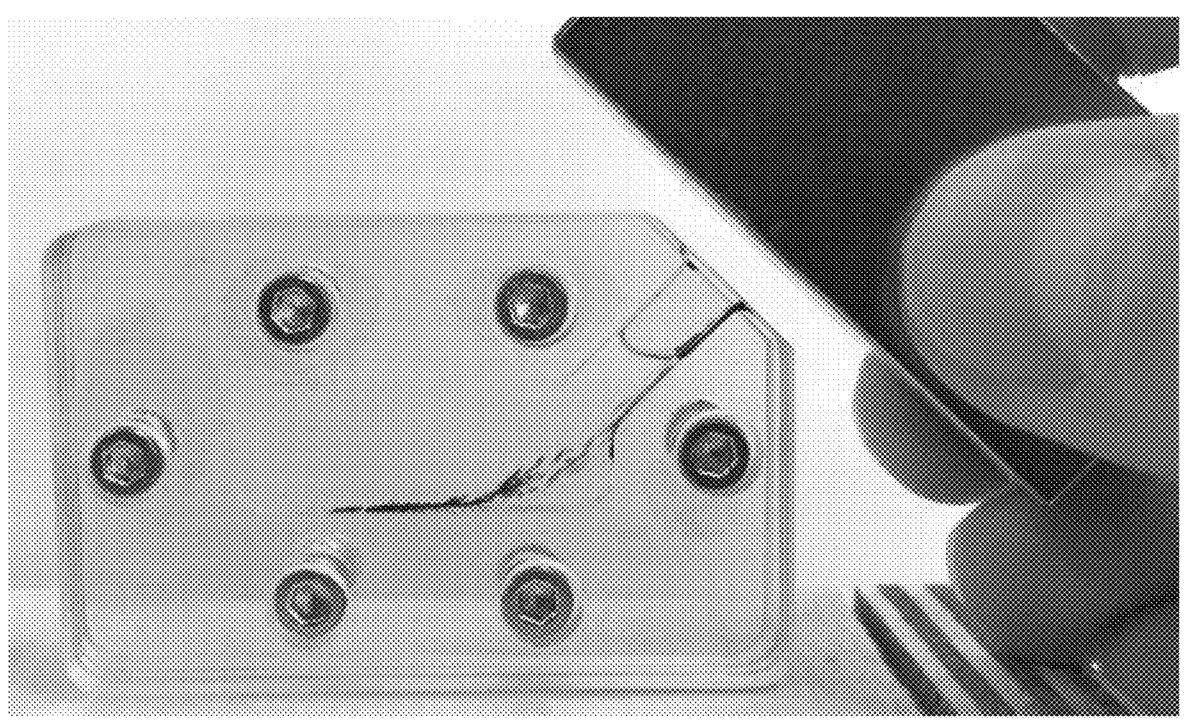
FIG. 9 depicts a first retrieval step in which beads are pulled into the model nasal passage with a large magnet positioned outside of the nasal model.
Figure 10:
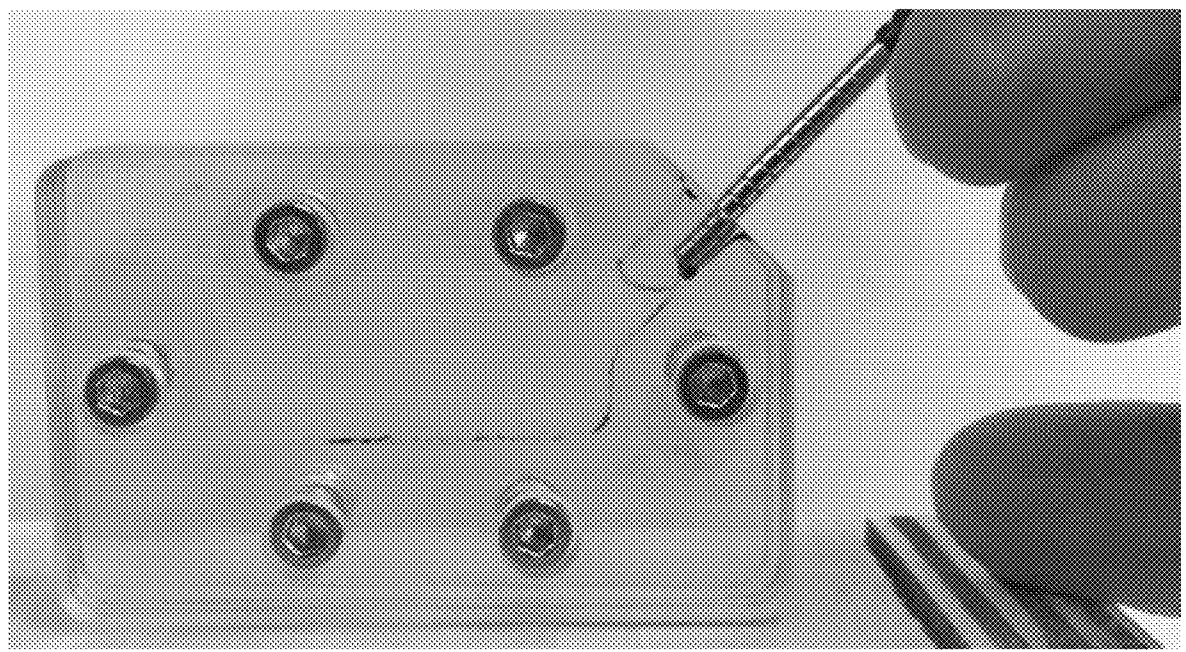
FIG. 10 depicts a second retrieval step in which beads are retrieved using small magnets in the model nasal passage.

Bead Retrieval using the Large Magnet first and then Small Magnets: The nasal model with a swab viscosity of 1 cP (water) was used to look at bead retrieval using a particular sequence of magnets: First, a large magnet outside the head was used to pull beads out of the olfactory cleft and into the nasal passage. Second, small magnets were used to retrieve the beads from the nasal passage. This was successful, as shown in FIG. 9 and FIG. 10.

Example 3: Housekeeping Biomarkers

Housekeeping biomarkers are those biomarkers that uniquely identify the collected fluid as containing CSF. Housekeeping biomarkers need to occur in CSF and not in any other part of the nasal passages (such as mucosa, saliva, blood from a cut, and so forth). Ideally, housekeeping biomarkers can also be measured using commonly available assays.

β-2-Transferrin: β-2-transferrin is a protein that occurs only in CSF. It is used to diagnose gross CSF leaks into the nasal cavity as a result of severe trauma.

Tau Protein (TAU): A recent paper (Oudart et. al. *Tau protein as a possible marker of cerebrospinal fluid leakage in cerebrospinal fluid rhinorrhoea: A pilot study*. Biochem Med (Zagreb). 2017 Oct. 15; 27 (3): 030703.) concluded that the measurement of TAU may reliably detect the presence of CSF in nasal discharge and signal the existence of a CSF leak.

Use of TAU as a Housekeeping and Diagnostic Biomarker: TAU may be used both as a housekeeping biomarker and as a diagnostic biomarker. When TAU is measured as a diagnostic biomarker, it may be unnecessary to separately measure it as a housekeeping biomarker.

Example 4: Diagnostic Biomarkers

Diagnostic biomarkers are those CSF biomarkers used to diagnose neurodegenerative diseases such as Alzheimer's Disease (AD). Ideally, diagnostic biomarkers can be measured using commonly available assays.

Example 4.1: Diagnostic Biomarkers Selected for Testing

Tau Protein (TAU): Tau is a protein that helps stabilize the internal skeleton of nerve cells (neurons) in the brain. This internal skeleton has a tube-like shape through which nutrients and other essential substances travel to reach different parts of the neuron. In Alzheimer's disease, an abnormal form of tau builds up and causes the internal skeleton to fall apart. These abnormal forms of tau protein cling to other tau proteins inside the neuron and form tau tangles. Tau tangles and amyloid-beta plaques-large accumulations of microscopic brain protein fragments that slow a person's ability to think and remember—are hallmarks of Alzheimer's disease. This example includes measurement of total tau (also written as t-tau), designated as TAU. Some portion of the total tau may be phosphorylated tau (also written as p-tau) and this version of tau is yet another marker for AD. However, p-tau was not used in this example.

Amyloid-β 42 Protein (AB42): The β-amyloid (sometimes referred to, confusingly, as amyloid-β) protein fragment involved in Alzheimer's comes in several different molecular forms that collect between neurons. It is formed from the breakdown of a larger protein, called amyloid precursor protein. One form, β-amyloid 42, is thought to be especially toxic. In the Alzheimer's brain, abnormal levels of β-amyloid 42 clump together to form plaques that collect between neurons and disrupt cell function.

The TAU:AB42 Ratio as a Diagnostic Indicator of Alzheimer's: While the individual concentrations of various CSF proteins have been used to help diagnose AD, the ratios between various concentrations have now been shown to better distinguish AD patients from other patients. One of the promising ratios is the TAU:AB42 ratio. In fact, a recent study indicates this particular ratio may have the best predictive value for AD diagnosis. TAU and AB42 were tested because TAU:AB42 is a very promising ratio. The necessary supplies (TAU protein, AB42 protein, ELISA measurement kits for both, and antibodies for both that could be attached to magnetic beads) were obtained, and allowed measurement of the concentrations of TAU and AB42 and calculation of the ratio between them.

Example 4.2: Human CSF vs Simulated CSF

It is sometimes more convenient to work with simulated CSF than human CSF. Creation of simulated CSF provides known concentrations of the biomarkers. Knowing the biomarker concentrations before measurement using the ELISA kits allows us to judge the measurement results.

Simulated CSF was made as follows:

start with PBS (Phosphate Buffered Saline) as the liquid then add biomarkers in a roughly physiological concentration, which for healthy patients is:

| | | |
|---|---|---|
| TAU | <300 pg/ml | 21-50 years old |
| TAU | <450 pg/ml | 51-70 years old |
| TAU | <550 pg/ml | 71-93 years old |
| AB42 | >500 pg/ml | for all ages |

Pooled human CSF was purchased from Innovative Research Inc (product IRHUCSF1ML). Using a total tau ELISA kit (details below) detection of tau protein within the limit of detection of the kit (10 pg/mL) was expected, but not realized. It was determined that single-donor samples are handled much more carefully than pooled samples, ie they are frozen quickly and normally do not go through multiple freeze-thaw cycles, unlike pooled samples.

Example 4.3: Liquid Swab Formulations

Multiple different liquid swab formulations were tested, all with a viscosity <65 cP because of a determination that the liquid swab is optimally delivered to the middle of the olfactory cleft when its viscosity stays in the 1-65 cP range. Good results have been obtained using glycerin+water as the formulation, so this was included along with the PEG+water formulations.

Throughout the various diagnostic marker experiments, the following swab formulations were used:

PEG+water @ 6 cP (1 part PEG: 3 parts water by weight or 0.25 PEG mass fraction)

PEG+water @ 39 cP (1 part PEG: 1 part water by weight or 0.50 PEG mass fraction)

GLY+water @ 2 cP (250 parts GLY: 1000 parts water by volume)

GLY+water @ 6 cP (800 parts GLY: 1000 parts water by volume)

GLY+water @ 40 cP (2500 parts GLY: 1000 parts water by volume)

Example 4.4: ELISA Measurement-Simulated CSF in Liquid Swabs

Purpose: This ELISA measurement provided validation on whether the ELISA can: (1) measure the biomarker concentration in simulated CSF; (2) measure the biomarker concentration in PEG+water swabs; and (3) measure the biomarker concentration in GLY+water swabs. This experiment does not include collection of CSF in the liquid swabs. This experiment allows for determination of whether the liquid swabs interfere with the ELISA measurement and thus includes addition of TAU directly to the liquid swabs.

Materials:

TAU ELISA=tau ELISA kit (Fisher/Invitrogen part #KHB4100)

TAU=tau-441 (1-421) protein (Sigma part #SRP0701)

PBS=Phosphate Buffered Saline, pH 7.4 (Sigma part #P3813-10PAK)

Figure 11:
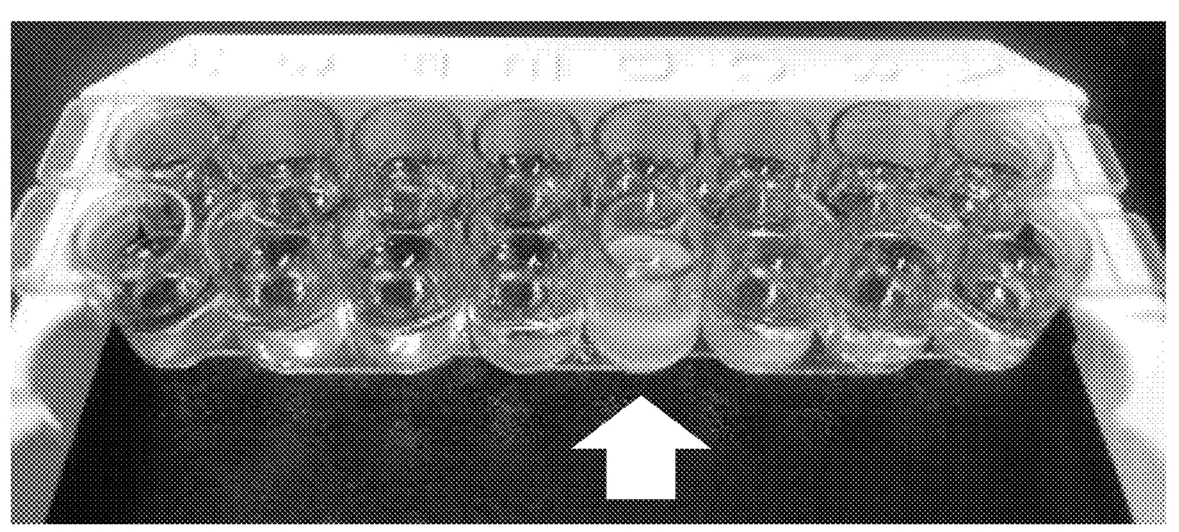
FIG. 11 depicts a number of sample wells including a cloudy well (see white arrow) with 39 cP PEG+a water swab.

Method: First, the following formulations were prepared:

simulated CSF was made by adding TAU to PBS at 100 pg/ml simulated CSF was made by adding TAU to PBS at 400 pg/ml 6 cP PEG swab was made and TAU was added at 400 pg/ml 39 cP PEG swab was made and TAU was added at 400 pg/ml 2 cP GLY swab was made and TAU was added at 400 pg/ml 40 cP GLY swab was made and TAU was added at 400 pg/ml Then the TAU concentrations in these 6 sample fluids were measured using the ELISA kit. During the ELISA kit procedure, it was observed that the well containing the 39 cP PEG swab had turned cloudy. See FIG. 11.

Figure 12:
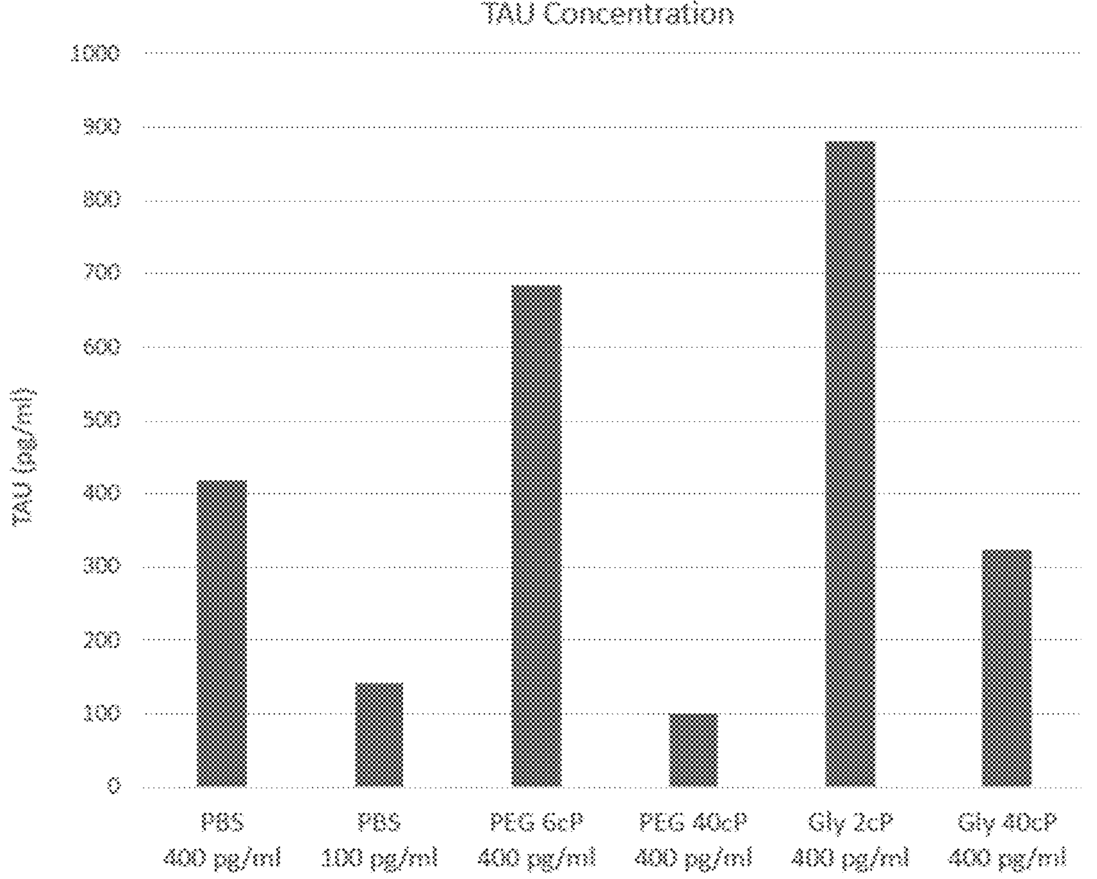
FIG. 12 depicts a graph of measured TAU concentrations in pure cerebrospinal fluid (CSF) and Liquid Swabs.

Discussion: Results are shown in FIG. 12. The measured tau concentrations in the 400 pg/ml and 100 pg/ml PBS samples correlated well with the known concentrations. Tau was measured in all liquid swabs, indicating that these swabs don't preclude the use of an ELISA kit measurement. Additionally:

Both lower viscosity swabs (6 cP PEG and 2 cP GLY) measured significantly above the 400 pg/ml at which they were created.

The higher viscosity 39 cP PEG swab had significant negative interference with the assay The higher viscosity 40 cP GLY swab measured reasonably well, ie close to the value measured in PBS.

Example 4.5: ELISA Measurement-Mixing CSF and Liquid Swabs

Purpose: This ELISA measurement investigated how best to mix the CSF into the liquid swab: ·CSF (ρ~1 g/ml) will always float on any practical liquid swab (ρ>1 g/ml)

To illustrate this, red dye was added to some of our simulated CSF and this CSF was added to a 6 cP PEG swab and a 39 cP PEG swab. See FIG. 13.

Materials:

TAU ELISA=tau ELISA kit (Fisher/Invitrogen part #KHB4100)

TAU=tau-441 (1-421) protein (Sigma part #SRP0701)

PBS=Phosphate Buffered Saline, pH 7.4 (Sigma part #P3813-10PAK)

BEADS=MagSi-DNA 3.0 μm silica-coated superparamagnetic beads (Magtivia part #MD0X022, purchased from Boca Scientific Inc, Dedham, MA. Boca part #MD01022)

Method: First Create all the Liquids:

make simulated CSF by adding TAU to PBS at 400 pg/ml make GLY swabs at 6 cP

Figure 13:
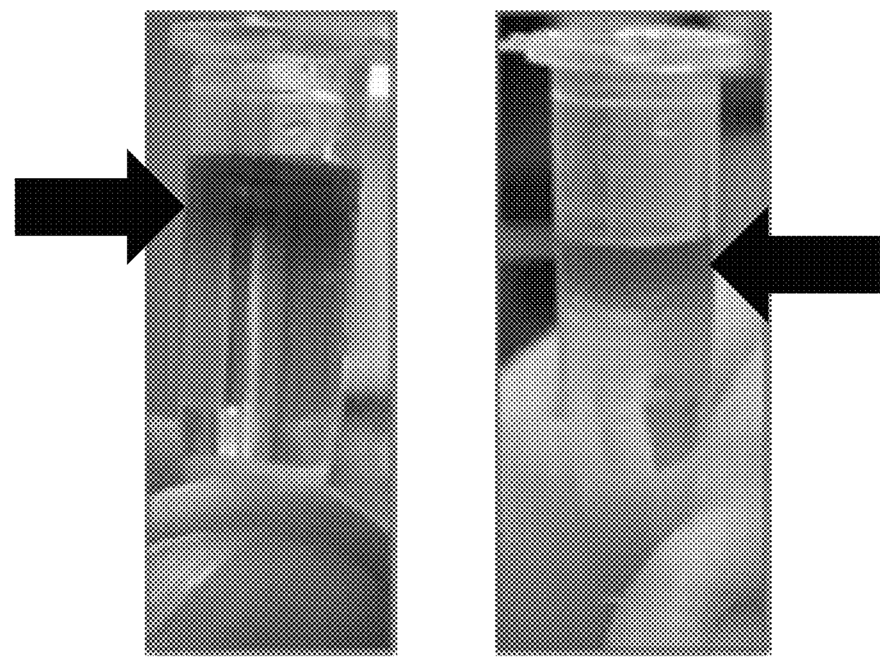
FIG. 13 depicts cerebrospinal fluid (CSF) floating on top of a 6 cP PEG swab (left) and on top of a 39 cP PEG swab (right). The floating CSF is marked with arrows.

Then prepare 3 microcentrifuge tubes much as shown in FIG. 13 above:

first add 350 μl of the GLY swab then add 50 μl of the simulated CSF

Then mix the CSF into the liquid swab in 3 different ways:

tube 1. don't mix at all, wait 5 min, then pipette out 50 μl of the lower liquid (swab) only this represents the worst mixing possible: no mixing at all the only way the TAU can enter the liquid swab is via diffusion, which is very slow carefully retrieving only liquid swab means that any TAU measured must have entered the liquid swab via diffusion tube 2. mix vigorously by repeatedly aspirating and dispensing the liquid in the tube with a pipette this represents the best mixing possible: vigorous mechanical mixing this should result in the highest possible measured TAU concentration note that vigorous mechanical mixing is likely not feasible in the olfactory cleft, as the space is narrow and the cribriform plate is fragile tube 3. add plain magnetic beads (3 μm diameter, no antibody coating), use magnet to move the beads up and down to mix the CSF into the liquid swab this represents a mixing method that may well be possible inside the olfactory cleft plain beads are used in this example but beads coated with antibodies to capture the biomarkers directly are also possible the mixing will not be as vigorous as in tube 2, and the measured TAU concentration is expected to lie between that measured in tubes 1 and 2

Figure 14:
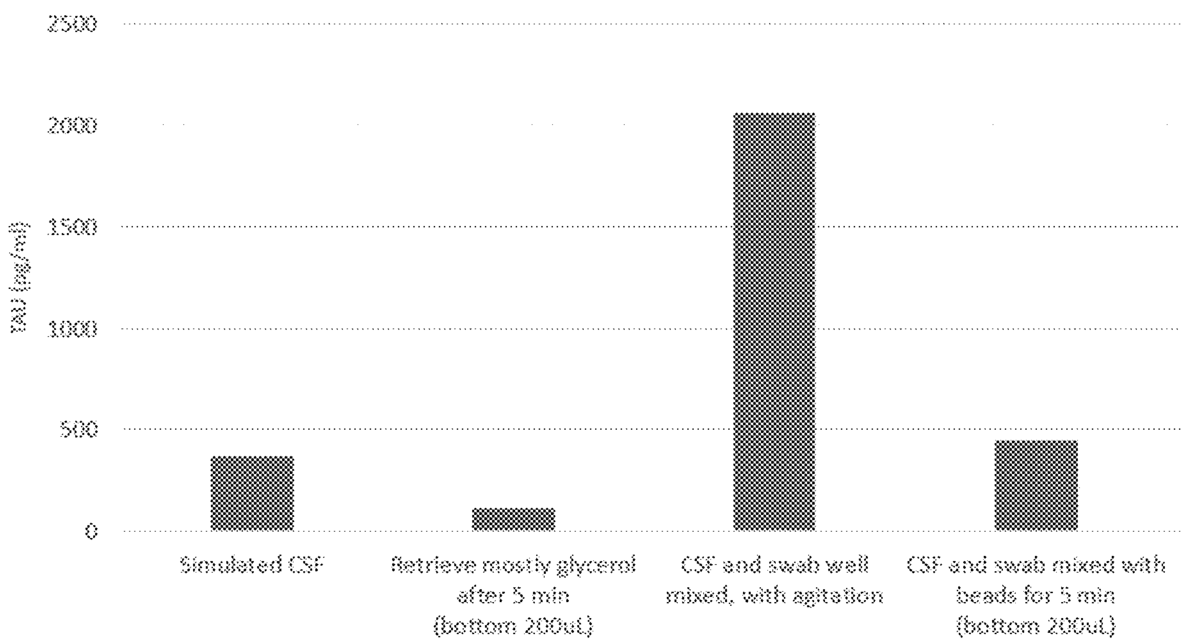
FIG. 14 depicts a graph of measured TAU concentrations vs mixing methods. The measurements correspond to simulated CSF 50 μL of PBS with 400 pg/mL TAU) sitting atop 350 μL of 6 cP glycerol liquid swab in a microcentrifuge tube.

Discussion: Results are shown in FIG. 14. Simulated CSF was measured first as a control. The ELISA correctly measured 400 pg/ml. The samples from the 3 tubes were then measured:

tube 1. no mixing as expected, this gave the lowest measured TAU concentration this reinforces the fact that diffusion alone is a poor way to get biomarkers into the swab tube 2. mix mechanically as expected, this gave the highest measured TAU concentration as with the first ELISA test, note that the measured TAU concentration with a GLY swab results in measured TAU concentrations well above the actual TAU concentration in the simulated CSF note that vigorous mechanical mixing is likely not feasible in the olfactory cleft, as the space is narrow and the cribriform plate is fragile tube 3. mix with magnetic beads as expected, the measured TAU concentration was between that measured in tubes 1 and 2 this illustrates that magnetic mixing increases biomarker capture efficiency

Example 4.6: ELISA Measurement: Magnetic Beads Coated with AB42 Antibody

This example relates to ELISA measurement to investigate the use of magnetic beads coated with antibodies to capture biomarkers.

Materials

ELISA=Human Amyloid Beta 42 ELISA Kit (Abcam part number AB289832)

AB42=Human Beta Amyloid (1-42) PTD Recombinant Protein (Invitrogen part #03111)

PBS=Phosphate Buffered Saline, pH 7.4 (Sigma part #P3813-10PAK)

BEADS=Dynabeads Protein G Immunoprecipitation Kit (Invitrogen part #10007D)

AB42 ANTIBODY=Anti-B-Amyloid Antibody, Mouse monoclonal (Sigma part #A3981)

Methods

Step 1: Prepare simulated CSF by adding AB42 to PBS at 450 pg/ml.

Step 2: Coat the beads with the AB42 antibodies per the Dynabeads kit instructions.

Step 3: Incubate the antibody-coated beads in 200 μl of the simulated CSF for 1 hour.

Step 4: Collect the beads by placing a magnet on outside of tube containing the simulated CSF+beads so that the beads inside the tube aggregate near the magnet. Pour off the liquid supernatant, and keep this supernatant for later testing in the ELISA kit to see how much AB42 protein was not collected by the beads.

Step 5: Remove captured AB42 protein from the antibodies on the beads using the low pH elution buffer provided in the Dynabeads kit, and add the eluted AB42 protein to 200 μl of PBS.

Step 6: Run the following sample liquids in the ELISA assay:

A. Simulated CSF to verify the AB42 concentration in that simulated CSF.
B. The AB42 protein eluted from the antibodies on the magnetic beads.
C. The supernatant containing all the AB42 protein NOT captured by the beads.

Results

Figure 15:
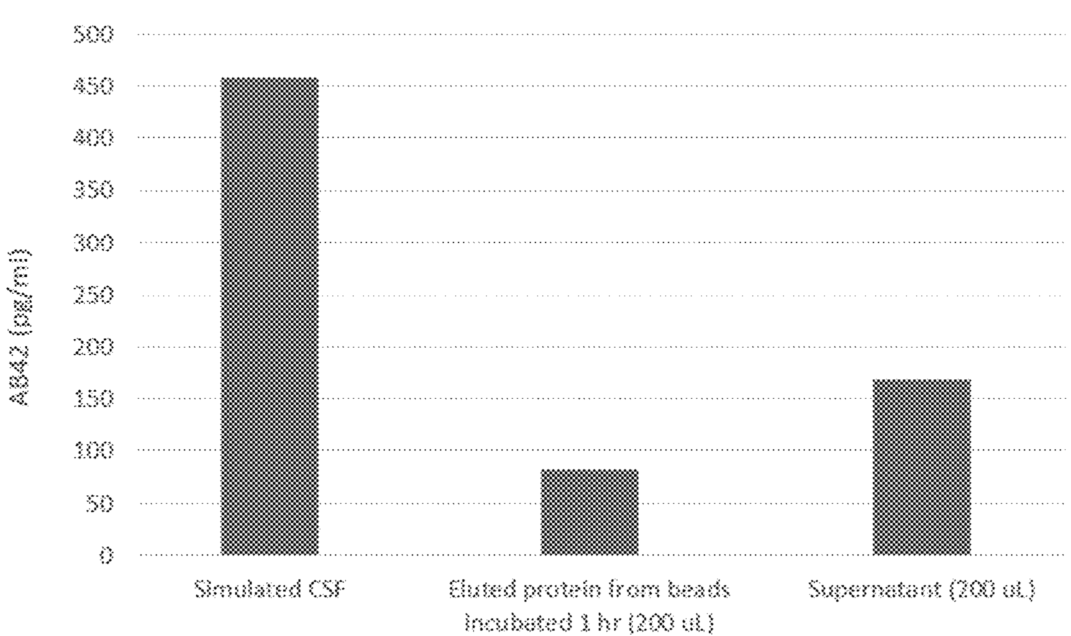
FIG. 15 depicts a graph of measured AB42 concentrations.

The measured AB42 concentration in the simulated CSF measured ~450 pg/ml. The protein eluted from the antibody-coated beads measured ~80 pg/ml. The supernatant measured ~150 pg/ml. See FIG. 15.

DISCUSSION

These results allow for comparison of the total amount of protein in the simulated CSF, the amount of that protein captured by the antibody-coated beads, and the amount left in the simulated CSF. The antibody-coated beads were placed in 200 μl of simulated CSF containing 450 pg/ml which means there was a total of 90 pg of AB42 protein.

The supernatant is the simulated CSF after the antibody-coated beads had picked up their AB42. The supernatant measured ~150 pg/ml, which is ⅓ of the original 450 pg/ml. This means that the antibody-coated beads picked up ⅔ of the available 90 pg of AB42 which is 60 pg of AB42.

If the elution step had removed 100% of the captured AB42 from the antibodies, all 60 pg of AB42 would have been added to the 200 μl of PBS, which should have measured as: 60 pg into 200 μl of PBS=300 pg/ml.

Only 80 pg/ml was measured in the eluted AB42 sample. This means that the elution step only removed 80/300=27% of the AB42 bound to the antibodies. This can be optimized to improve protein recovery.

Example 4.7: ELISA Measurement-Capture TAU with Magnetic Beads

Purpose: This ELISA measurement investigated the use of magnetic beads coated with antibodies to capture TAU protein.

Materials

TAU ELISA=tau ELISA kit (Fisher/Invitrogen part #KHB0041)

TAU=tau-441 (1-421) protein (Sigma-Aldrich part #SRP0701)

TAU ANTIBODY 1=tau monoclonal antibody (EPR22524-95) (Abcam part #ab254256)

TAU ANTIBODY 2=tau monoclonal antibody (EPR25205-233) (Abcam part #ab308439)

TAU ANTIBODY 3=tau monoclonal antibody (Tau-5) (Fisher/Invitrogen part #AHB0042)

PBS=Phosphate Buffered Saline, pH 7.4 (Sigma part #P3813-10PAK)

BEADS=Dynabeads protein G immunoprecipitation kit (Fisher/Invitrogen part #10007D)

TRIS-HCL=1M Tris-HCl buffer, pH 7.5 (Fisher/Invitrogen part #15567027)

Method

First create all the liquids: make simulated CSF by adding TAU to PBS at 400 pg/ml Then coat a first set of beads with TAU ANTIBODY 1, a second set of beads with TAU ANTIBODY 2, and a third set of beads with TAU ANTIBODY 3 per the Dynabeads kit instructions.

Then incubate the 3 separate sets of antibody-coated beads in 3 separate aliquots of simulated CSF:

add TAU ANTIBODY 1-coated beads to 400 pl of simulated CSF add TAU ANTIBODY 2-coated beads to 400 pl of simulated CSF add TAU ANTIBODY 3-coated beads to 400 pl of simulated CSF leave for 1 hour After incubation, collect the beads:

place magnet on outside of tube containing the simulated CSF+beads the beads inside the tube aggregate near the magnet remove the liquid, which is now called the supernatant keep this supernatant for later testing in the ELISA kit to see how much TAU protein was NOT collected by the beads Then remove captured TAU protein from the antibodies on the beads:

elute (remove) captured TAU protein from the antibodies on the beads using the low pH elution buffer provided in the Dynabeads kit re-suspend the eluted TAU protein in 120 pl of TRIS-HCL (total volume)

Then run the following sample liquids in the ELISA assay:

simulated CSF to verify the TAU concentration in the simulated CSF the TAU protein eluted from the antibodies on the beads the supernatant containing all the TAU protein NOT captured by the beads Results The measured TAU concentration in the simulated CSF measured ~385 pg/ml.

The protein eluted from the ANTIBODY 1-coated beads measured ~80 pg/ml.

The supernatant measured ~15 pg/ml.

The protein eluted from the ANTIBODY 2-coated beads measured ~305 pg/ml.

The supernatant measured ~60 pg/ml.

The protein eluted from the ANTIBODY 3-coated beads measured ~140 pg/ml.

Figure 16:
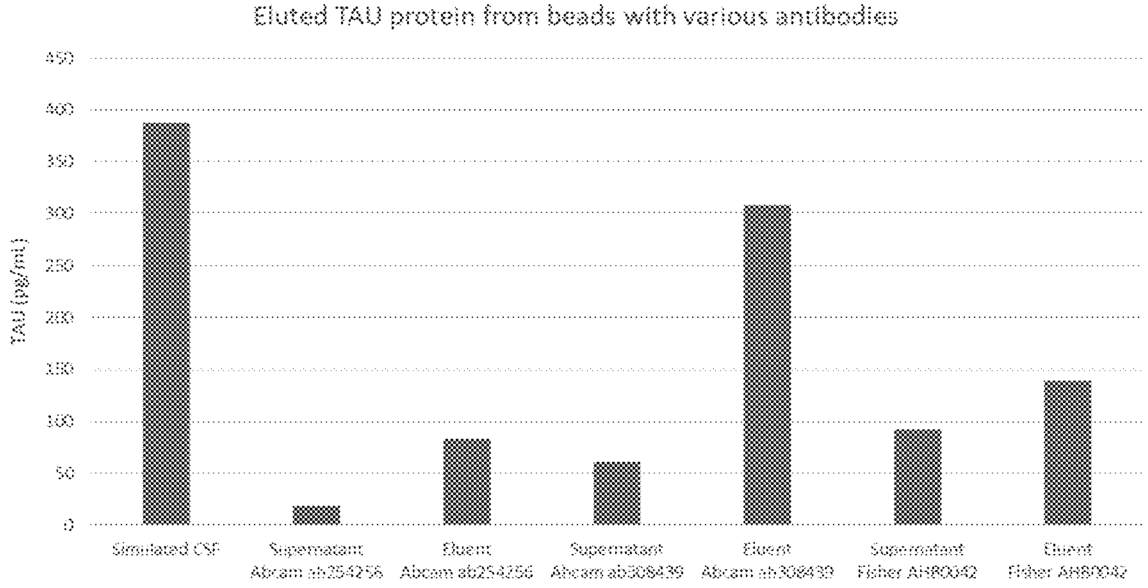
FIG. 16 depicts a graph of measured TAU concentrations corresponding to eluted TAU protein from beads with various antibodies.

The supernatant measured ~90 pg/ml. See FIG. 16

DISCUSSION

The measured TAU concentration in the simulated CSF was very close to the 400 pg/ml concentration at which it was prepared. This indicates that the CSF was properly prepared and the ELISA kit is working as it should.

All 3 sets of antibody-coated beads removed at least 75% of the TAU protein because all 3 supernatants measured <100 pg/ml, indicating that >300 pg/ml had been removed from the simulated CSF by the beads.

While the supernatant measurements indicate that the antibody-coated beads removed at least 300 pg/ml from the simulated beads, the 3 eluents measured significantly less than 300 pg/ml. This is partly due to the fact that not all protein is recovered from the antibodies and partly due to the decision of how much volume of liquid (TRIS-HCL) to re-suspend (place) the eluted proteins in.

These results may be interpreted by considering the total amount of protein in the simulated CSF and then determining how much of that protein was captured by the antibody-coated beads and how much was left in the simulated CSF.

Consider the best performing antibody, which was TAU ANTIBODY 2 (Abcam part #ab308439): The antibody-coated beads were placed in 400 pl of simulated CSF containing 400 pg/ml, which means there was a total of 160 pg of TAU in the sample.

The supernatant is the simulated CSF after the antibody-coated beads picked up their TAU. The supernatant measured ~60 pg/ml in the 400 pl, which means there was a total of 24 pg of TAU left in the supernatant.

Calculation of how much TAU was picked up by the antibody-coated beads: The antibody-coated beads picked up 160 pg-24 pg=136 pg of TAU. The TAU was then eluted from the antibodies and the eluted TAU was re-suspended into 120 pl of PBS.

If the elution step had removed 100% of the 136 pg of captured TAU from the antibodies, all 136 pg would have been added to the 120 pl of PBS, which should have measured as: 136 pg into 120 pl of PBS=1133 pg/ml But only 305 pg/ml was measured in the eluted TAU sample. This means that: The elution step only removed 305/1133=27% of the TAU bound to the antibodies.

This is the same elution efficiency obtained in the AB42 ELISA test (see Example 4.6).

Example 4.8: ELISA Measurement-TAU:AB42 Ratios with Magnetic Beads 1

Purpose: This ELISA measurement investigated the use of magnetic beads coated with antibodies to capture both TAU and AB42 protein and so measure TAU:AB42 ratios.

Materials

- TAU ELISA=tau ELISA kit (Fisher/Invitrogen part #KHB0041)
- TAU=tau-441 (1-421) protein (Sigma-Aldrich part #SRP0701)
- TAU ANTIBODY=tau monoclonal antibody (EPR25205-233) (Abcam part #ab308439)
- AB42 ELISA=amyloid beta 42 ELISA kit (Abcam part number AB289832)
- AB42=amyloid beta protein (AB42 ELISA kit protein standard)
- AB42 ANTIBODY=amyloid beta monoclonal antibody (Sigma part #A3981)
- PBS=Phosphate Buffered Saline, pH 7.4 (Sigma part #P3813-10PAK)
- BEADS=Dynabeads protein G immunoprecipitation kit (Fisher/Invitrogen part #10007D)
- TRIS-HCL=1M Tris-HCl buffer, pH 7.5 (Fisher/Invitrogen part #15567027)

Method

Create the simulated CSF with various TAU:AB42 ratios by adding the proteins to PBS:

| | | |
|---|---|---|
| CSF 1 = TAU at 500 pg/ml | and AB42 at 333 pg/ml | for a 1.5 TAU:AB42 ratio |
| CSF 2 = TAU at 1000 pg/ml | and AB42 at 333 pg/ml | for a 3.0 TAU:AB42 ratio |
| CSF 3 = TAU at 1500 pg/ml | and AB42 at 333 pg/ml | for a 4.5 TAU:AB42 ratio |

Separately coat a first set of beads with TAU ANTIBODY and a second set of beads with AB42 ANTIBODY per the Dynabeads kit instructions. After coating, mix both sets of beads together.

Add the bead mixture to the simulated CSF and incubate:

- add ⅓ of the bead mixture to CSF 1
- add ⅓ of the bead mixture to CSF 2
- add ⅓ of the bead mixture to CSF 3
- incubate for 1 hour After incubation, collect the beads:

- place magnet on outside of tube containing the simulated CSF+beads
- the beads inside the tube aggregate near the magnet
- remove the liquid, which is now called the supernatant
- keep this supernatant for later testing in the ELISA kit to see how much TAU and AB42 protein was NOT collected by the beads After the incubation period, remove captured TAU and AB42 protein from the antibodies on the beads using the low pH elution buffer provided in the Dynabeads kit:

- elute captured TAU and AB42 protein from CSF 1
- re-suspend the eluted TAU and AB42 protein in 190 µl of TRIS-HCL
- call this RE-SUSPENSION 1
- elute captured TAU and AB42 protein from CSF 2
- re-suspend the eluted TAU and AB42 protein in 190 µl of TRIS-HCL
- call this RE-SUSPENSION 2
- elute captured TAU and AB42 protein from CSF 3
- re-suspend the eluted TAU and AB42 protein in 190 µl of TRIS-HCL
- call this RE-SUSPENSION 3

Then run the re-suspensions in the ELISA assays:

- measure TAU protein eluted from CSF 1 by running RE-SUSPENSION 1 in the TAU ELISA kit
- measure TAU protein eluted from CSF 2 by running RE-SUSPENSION 2 in the TAU ELISA kit
- measure TAU protein eluted from CSF 3 by running RE-SUSPENSION 3 in the TAU ELISA kit
- measure AB42 protein eluted from CSF 1 by running RE-SUSPENSION 1 in the AB42 ELISA kit
- measure AB42 protein eluted from CSF 2 by running RE-SUSPENSION 2 in the AB42 ELISA kit
- measure AB42 protein eluted from CSF 3 by running RE-SUSPENSION 3 in the AB42 ELISA kit Then use the TAU and AB42 measurements to calculate the TAU:AB42 ratios.

Results

Figure 17:
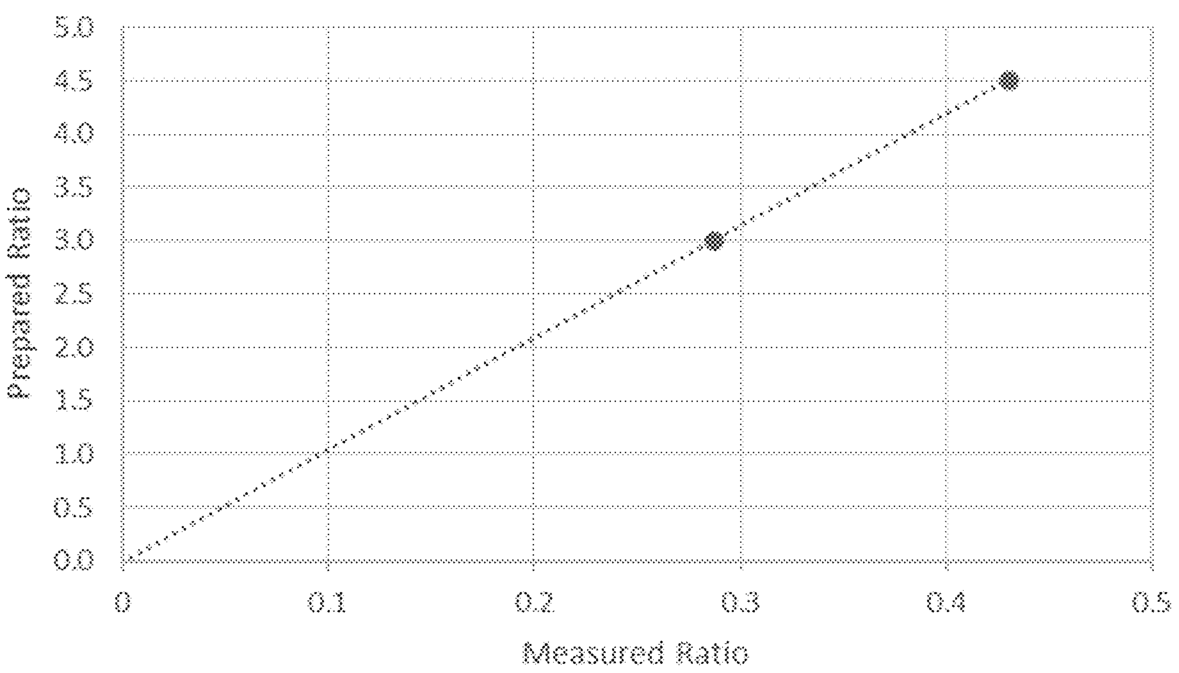
FIG. 17 depicts a graph of prepared vs. measured TAU: AB42 ratios.

For CSF 1, no meaningful ratio was obtained. For CSF 2, the TAU measured 106 pg/ml and the AB42 measured 369 pg/ml for a 0.287 TAU:AB42 ratio. For CSF 3, the TAU measured 179 pg/ml and the AB42 measured 416 pg/ml for a 0.430 TAU:AB42 ratio. See FIG. 17

DISCUSSION

While only two of the three prepared ratios were successfully measured, an extra data point may be assumed because dropping the TAU to 0 pg/ml would lead to a TAU:AB42 ratio=0 and, indeed, a linear fit of the two data points does go through the origin.

This experiment mixed TAU protein, AB42 protein, magnetic beads, TAU antibodies and AB42 antibodies together in simulated CSF. Successful collection, elution, and measurement of both TAU protein and AB42 protein is extremely positive. None of the proteins, beads and antibodies interfered with one another:

The presence of TAU protein did not interfere with the binding of the AB42 protein to its antibody and vice versa.

The presence of TAU protein did not interfere with the elution of the AB42 protein from its antibody and vice versa.

The measured TAU:AB42 ratios were different (approximately 10× lower) than the prepared ratios. This may be because:

Different antibodies have different protein binding affinities. During the incubation step, the TAU antibody will capture a certain percentage of the available TAU protein, while the AB42 antibody will capture a different percentage of the available AB42 protein. So the ratio is already different after the protein capture step.

Different antibodies will have different elution characteristics. During the protein elution step, the TAU antibody will release a certain percentage of its captured TAU protein, while the AB42 antibody will release a different percentage of its captured AB42 protein. So the ratio changes again.

The difference between the measured ratio and the actual ratio may be dealt with by calibration of the ratio measurement:

prepare sample fluids with known TAU:AB42 ratios measure the TAU:AB42 ratios in the prepared sample fluids calculate the calibration factor(s) that convert measured ratios into actual ratios:

For example, in this case:

for CSF 2, the prepared ratio=3.0 and the measured ratio=0.287, which is 10.45× smaller for CSF 3, the prepared ratio=4.5 and the measured ratio=0.430, which is 10.47× smaller Since the linear fit line passed through the origin, there is no need for an offset term and the calibration equation simplifies to:

actual TAU:AB42 ratio=10.46× measured TAU:AB42 ratio

Example 4.9: ELISA Measurement—TAU:AB42 Ratios with Magnetic Beads

Purpose: This is the second ELISA measurement of TAU:AB42 ratios. The first ELISA measurement of TAU:AB42 ratios (see Example 4.8) used the AB42 protein that comes with the AB42 ELISA kit because this lyophilized AB42 protein reliably re-constitutes and shows accurate signal on the kit. Later measurements used Abcam part number AB120301.

Materials

TAU ELISA=tau ELISA kit (Fisher/Invitrogen part #KHB0041)

TAU=tau-441 (1-421) protein (Sigma-Aldrich part #SRP0701)

TAU ANTIBODY=tau monoclonal antibody (EPR25205-233) (Abcam part #ab308439)

AB42 ELISA=amyloid beta 42 ELISA kit (Abcam part number AB289832)

AB42=amyloid beta (1-42) protein (Abcam part number AB120301)

AB42 ANTIBODY=amyloid beta monoclonal antibody (Sigma part #A3981)

PBS=Phosphate Buffered Saline, pH 7.4 (Sigma part #P3813-10PAK)

BEADS=Dynabeads protein G immunoprecipitation kit (Fisher/Invitrogen part #10007D)

TRIS-HCL=1M Tris-HCl buffer, pH 7.5 (Fisher/Invitrogen part #15567027)

Method

Prepare the simulated CSF with various TAU:AB42 ratios by adding the proteins to PBS:

| | | |
|---|---|---|
| CSF 0 = TAU at 0 pg/ml | and AB42 at 1000 pg/ml | for a 0 TAU:AB42 ratio |
| CSF 1 = TAU at 250 pg/ml | and AB42 at 1000 pg/ml | for a 0.25 TAU:AB42 ratio |
| CSF 2 = TAU at 1000 pg/ml | and AB42 at 1000 pg/ml | for a 1.00 TAU:AB42 ratio |
| CSF 3 = TAU at 2000 pg/ml | and AB42 at 1000 pg/ml | for a 2.00 TAU:AB42 ratio |

Separately coat a first set of beads with TAU ANTIBODY and a second set of beads with AB42 ANTIBODY per the Dynabeads kit instructions. After coating, mix both sets of beads together.

Add the bead mixture to the simulated CSF and incubate:

add ⅓ of the bead mixture to CSF 1 add ⅓ of the bead mixture to CSF 2 add ⅓ of the bead mixture to CSF 3 incubate for 1 hour

After incubation, collect the beads:

place magnet on outside of tube containing the simulated CSF+beads the beads inside the tube aggregate near the magnet remove the liquid, which is now called the supernatant keep this supernatant for later testing in the ELISA kit to see how much TAU and AB42 protein was NOT collected by the beads After the incubation period, remove captured TAU and AB42 protein from the antibodies on the beads using the low pH elution buffer provided in the Dynabeads kit:

elute captured TAU and AB42 protein from CSF 1 re-suspend the eluted TAU and AB42 protein in 220 μl of TRIS-HCL call this RE-SUSPENSION 1 elute captured TAU and AB42 protein from CSF 2 re-suspend the eluted TAU and AB42 protein in 220 μl of TRIS-HCL call this RE-SUSPENSION 2 elute captured TAU and AB42 protein from CSF 3 re-suspend the eluted TAU and AB42 protein in 220 μl of TRIS-HCL call this RE-SUSPENSION 3

Then run the re-suspensions in the ELISA assays:

measure TAU protein eluted from CSF 1 by running RE-SUSPENSION 1 in the TAU ELISA kit measure TAU protein eluted from CSF 2 by running RE-SUSPENSION 2 in the TAU ELISA kit measure TAU protein eluted from CSF 3 by running RE-SUSPENSION 3 in the TAU ELISA kit measure AB42 protein eluted from CSF 1 by running RE-SUSPENSION 1 in the AB42 ELISA kit measure AB42 protein eluted from CSF 2 by running RE-SUSPENSION 2 in the AB42 ELISA kit measure AB42 protein eluted from CSF 3 by running RE-SUSPENSION 3 in the AB42 ELISA kit Then use the TAU and AB42 measurements to calculate the TAU:AB42 ratios.

Results

The TAU protein gave good results but the AB42 protein provided poor signals.

Figure 18:
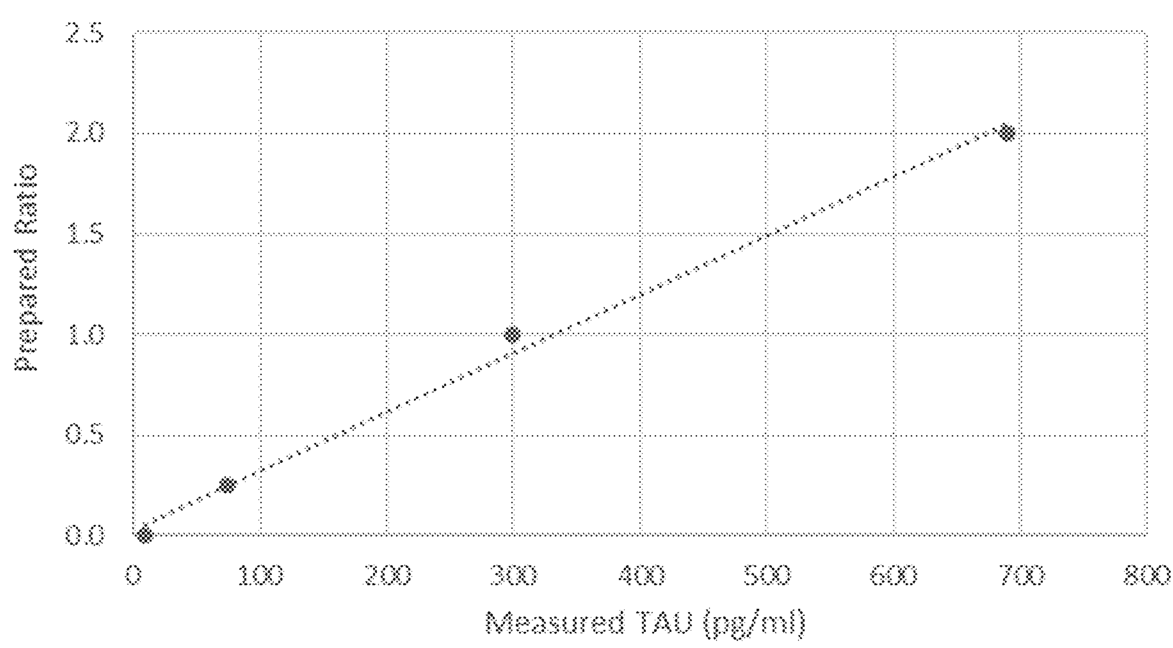
FIG. 18 depicts a graph of prepared ratio vs. measured TAU concentrations.

For the TAU protein, the results were as follows:

for CSF 0, the TAU measured 9 pg/ml for CSF 1, the TAU measured 74 pg/ml for CSF 2, the TAU measured 299 pg/ml for CSF 3, the TAU measured 689 pg/ml Even though the AB42 protein provided no appreciable signal, the known TAU:AB42 ratios at which the CSF was prepared can be plotted versus the measured TAU protein concentrations (See FIG. 18):

for CSF 0, the prepared ratio=0.00 and the TAU measured 9 pg/ml for CSF 1, the prepared ratio=0.25 and the TAU measured 74 pg/ml for CSF 2, the prepared ratio=1.00 and the TAU measured 299 pg/ml for CSF 3, the prepared ratio=2.00 and the TAU measured 689 pg/ml Discussion: This example demonstrated that TAU protein eluted from magnetic beads is strongly correlated with TAU protein concentration in the original sample (in which the beads were incubated), and over a broad range of concentrations (from 0-2000 pg/ml) which covers the entire physiological range (and beyond) of TAU protein concentration in CSF. When the 2 data points from the previous experiment (see Example 4.8) are considered as well, the correlation covers 6 steps across this 0-2000 pg/ml range. This is outstanding, as such a strong correlation—or, for that matter, any correlation at all—was unexpected. For example, the beads could have saturated with TAU protein at some concentration, after which the eluted protein concentrations would plateau. Considering both experiments, the above correlation between eluted TAU and TAU concentration in the original sample exists in the presence of two substantially different concentrations of AB42 (333 and 1,000 pg/ml). If the AB42 signal had not been corrupted, it most likely would have been constant and demonstrated preservation of the ratio. The next step is to vary both the AB42 and the TAU concentrations in the simulated CSF, not just the TAU concentrations.

Example 4.10: ELISA Measurement-AB42 in Mucus

Purpose: This is the first ELISA measurement of protein in the presence of mucus. This experiment allowed determination of the effect of a large amount of mucus on the ability to detect protein. Magnetic beads were not used.

Materials

AB42 ELISA=amyloid beta 42 ELISA kit (Abcam part number AB289832)

AB42=amyloid beta (1-42) protein from the ELISA kit above

PBS=Phosphate Buffered Saline, pH 7.4 (Sigma part #P3813-10PAK)

MUCUS=artificial nasal mucus, 3000-5000 cP (Biochemazone part number BZ253)

Method

First prepare a sample having only PBS as the liquid component. This is the usual simulated CSF: simulated CSF=PBS with AB42 at 700 pg/ml Then prepare a sample having only mucus as the liquid component. This extreme case determines the effect of 100% mucus on protein measurement. simulated MUCUS=MUCUS with AB42 at 700 pg/ml Now incubate these samples for different lengths of time:

| | | |
|---|---|---|
| simulated CSF | incubated for 1 hour | prior to measurement by ELISA |
| simulated MUCUS | incubated for 10 minutes | prior to measurement by ELISA |
| simulated MUCUS | incubated for 1 hour | prior to measurement by ELISA |

Measure AB42 concentrations using the AB42 ELISA kit.

Results

Figure 19:
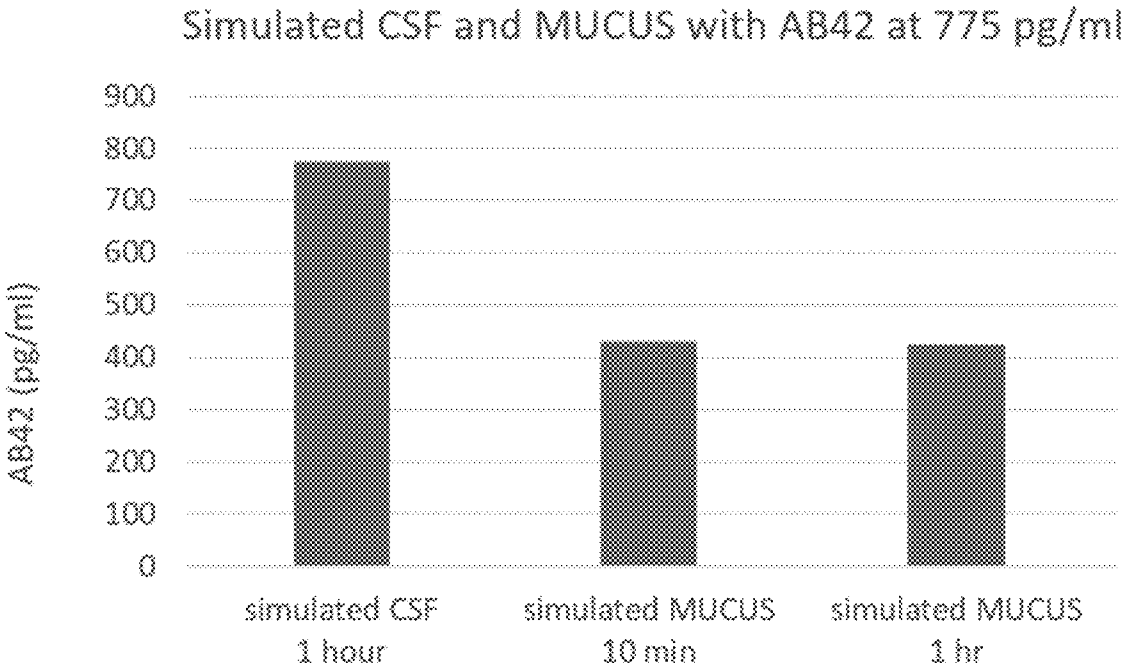
FIG. 19 depicts a graph of AB42 measurements in simulated CSF vs. simulated mucus.

The simulated CSF measured 775 pg/ml, close to the targeted AB42 concentration of 700 pg/ml. See FIG. 19. The simulated MUCUS samples both measured just over 400 pg/ml, or roughly half the prepared concentration.

Discussion: The MUCUS had the effect of decreasing the apparent AB42 concentration. Both MUCUS samples measured the same concentration, likely meaning the measurement was repeatable and unaffected by time of AB42 residence in MUCUS. If the AB42 were actively being digested by proteases in the MUCUS, one would expect the two measured concentrations to differ. This further suggests that the decrease in signal relative to that measured in simulated CSF is likely a matrix effect (ie the viscous MUCUS itself causes a repeatable decrease in signal from the ELISA kit). This is not a problem, and such an effect was seen in a previous experiment (see Example 4.4) where the apparent TAU concentration was decreased by high-viscosity PEG and glycerol liquid swab formulations.

Interestingly, the signal-suppressing effect of viscosity appeared to be much lower in MUCUS than in PEG or glycerol. PEG and glycerol were only tested up to 40 cP, whereas the synthetic MUCUS is approximately 4,000 cP (100 times greater), according to the manufacturer.

Example 5: Magnetic Bead Toxicity

This example relates to safety and toxicity of magnetic beads, particularly as it pertains to magnetic beads held in a liquid swab deposited into the olfactory cleft.

Magnetic Beads: The beads used in the examples above are superparamagnetic beads. Such beads exhibit magnetic behavior only in the presence of a magnetic field. The magnetic behavior disappears upon removal of the magnetic field.

Magnetism only in the presence of an external magnetic field is an attractive feature in the life sciences, as the beads may be gathered or displaced when needed by the introduction of a magnetic field but otherwise left free to move about. Furthermore, permanent (or even temporary) retention of magnetization could add additional health risks in vivo (eg pinching thin membranes within the body between two magnetic beads attracting one another, which could both damage the membrane and—if magnetization were permanent—potentially eliminate the possibility of expulsion from the body). The lack of such scenarios, their generally high biocompatibility, and a number of other aspects make superparamagnetic beads very useful tools in medical devices.

The shorter terms 'magnetic beads' or simply 'beads' are both used to refer to paramagnetic beads and to superparamagnetic beads. The term 'superparamagnetic' refers to a class of paramagnetic beads comprised of a material that has a particularly high magnetic response to external magnetic fields (technically, the magnetic susceptibility of superparamagnetic beads is higher than that of other paramagnetic beads).

The beads used to collect TAU and AB42 protein (see Example 4) are 2.8 μm diameter Dynabeads, which are superparamagnetic iron oxide beads covered with an inert polymer shell. These particular Dynabeads have the polymer shell coated with G protein. The G protein can be used to attach any antibody that couples to G protein. The examples above include versions of TAU and AB42 antibodies that couple well to G protein.

The beads used to study the movement of beads in liquid swabs (see Example 2.2) were very large (50 μm diameter) superparamagnetic iron oxide beads covered in an inert silica shell.

Bead coatings are frequently used to decrease the in vivo exposure to the internal magnetic material (typically iron oxide), and to impart a desired function (including antibody binding, dissolvable pharmaceutical layers, and improved contrast for various imaging techniques).

Iron oxide particles such as magnetite ($Fe_3O_4$) or its oxidized and more stable form of maghemite ($\gamma$-$Fe_2O_3$) are superior to other metal oxide particles in terms of biocompatibility and stability and are, by far, the most commonly employed magnetic particles for biomedical applications. Iron oxide is eventually broken down to form blood hemoglobin.

Additional Examples

Magnetic Beads in the Liquid Swab: Adding magnetic beads into a liquid swab can aid biomarker collection. The magnetic beads in the liquid swab can be used to mix the CSF into the liquid swab and/or directly capture biomarkers from the CSF. CSF is expected to float on top of the denser liquid swab. Magnetic beads in the liquid swab can help overcome this stratification and help retrieve the CSF biomarkers.

Mixing without Directly Capturing Biomarkers: Plain magnetic beads that are not coated with antibodies may be used. A moving magnetic field could move the plain beads around to actively mix the CSF into the liquid swab. Such mixing would increase the volume of CSF collected with the liquid swab upon retrieval of the liquid swab. Plain beads do not need any of the special coatings that are required to bind antibodies; they are free to be coated with a wide variety of inert coatings to, for example, reduce toxicity.

Directly Capturing Biomarkers without Mixing: Magnetic beads coated with antibodies may be used to directly capture biomarkers. A static magnetic field could pull the beads to the top of the olfactory cleft where they could come into direct contact with the CSF floating on the liquid swab. Biomarkers in the CSF could then be captured by the antibody-coated beads.

Directly Capturing Biomarkers+Mixing: Magnetic beads coated with antibodies could directly capture biomarkers. A moving magnetic field could move the beads around to actively mix the CSF into the liquid swab. Such mixing increases the contact between the biomarkers and the antibody-coated beads, maximizing the biomarker capture efficiency.

Biomarker Concentration and Washing: After liquid swab retrieval, magnetic beads coated with antibodies could be used to concentrate the biomarkers (collect liquid swab in a vessel, pull beads into a single spot with a magnet, then pour off liquid swab). Similarly, the magnetic beads can be washed (to remove enzymes that could damage the biomarkers) and the wash fluid poured off.

Biomarker Elution and Analysis: After washing, the biomarkers can be eluted (removed) from the antibodies and analyzed immediately or frozen for later analysis.

Keep Biomarkers on Beads: The biomarkers bound to the antibodies may be kept on the magnetic beads. Lateral flow immunoassays use antibodies attached to beads, including magnetic beads. The complete bead-antibody-biomarker complex may be fed directly into a lateral flow strip for a very inexpensive analysis. While many lateral flow tests are qualitative, there are ways to make them more quantitative, including the use of instruments that more accurately measure the quantity of beads captured at the test and control lines.

Enumerated Embodiments

Enumerated embodiment 1. A method of collecting biological material from a targeted region of a subject, the method comprising:
  - a. delivering a magnetic formulation comprising a plurality of magnetic particles to the targeted region of a subject, wherein the magnetic formulation is configured to capture the biological material; and
  - b. retrieving at least a portion of the magnetic formulation from the targeted region, thereby collecting any biological material captured by the portion of the magnetic formulation.

Enumerated embodiment 2. The method of any one of the preceding embodiments, wherein the targeted region is an olfactory region of the subject or a sub-region of the nasal cavity.

Enumerated embodiment 3. The method of any one of the preceding embodiments, wherein the sub-region is a nasal turbinate, a nasopharynx, or a sub-region of a nasal lymphatic system.

Enumerated embodiment 4. The method of any one of the preceding embodiments, wherein the magnetic particles are paramagnetic, diamagnetic, or ferromagnetic.

Enumerated embodiment 5. The method of any one of the preceding embodiments, wherein the formulation comprises a liquid suspension.

Enumerated embodiment 6. The method of any one of the preceding embodiments, wherein the biological material is captured from cerebrospinal fluid (CSF).

Enumerated embodiment 7. The method of any one of the preceding embodiments, wherein the magnetic particles are non-coated.

Enumerated embodiment 8. The method of any one of the preceding embodiments, wherein the magnetic particles are coated with or coupled to one or more antibodies configured to bind to a selected biological material.

Enumerated embodiment 9. The method of any one of the preceding embodiments, wherein each magnetic particle is coated with or coupled to a single antibody.

Enumerated embodiment 10. The method of any one of the preceding embodiments, wherein each magnetic particle is coated with or coupled to multiple antibodies.

Enumerated embodiment 11. The method of any one of the preceding embodiments, wherein analysis of the captured biological material provides a quantitative value for a concentration of tau protein, a concentration of beta-amyloid, or a ratio thereof.

Enumerated embodiment 12. The method of any one of the preceding embodiments, wherein analysis of the captured biological material provides a quantitative value for a ratio of tau protein and beta-amyloid 42, thereby enabling a diagnosis of Alzheimer's disease.

Enumerated embodiment 13. The method of any one of the preceding embodiments, additionally comprising eluting the captured biological material from the magnetic particles, and then analyzing the eluted biological material.

Enumerated embodiment 14. The method of any one of the preceding embodiments, wherein the biological material is analyzed via an enzyme-linked immunosorbent assay (ELISA).

Enumerated embodiment 15. The method of any one of the preceding embodiments, additionally comprising analyzing the captured biological material as a protein-bead complex.

Enumerated embodiment 16. The method of any one of the preceding embodiments, wherein the magnetic particles or protein-bead complex is washed and/or frozen prior to analysis of the captured biological material.

Enumerated embodiment 17. The method of any one of the preceding embodiments, wherein the biological material is analyzed via a self-administered test.

Enumerated embodiment 18. The method of any one of the preceding embodiments, wherein the biological material is analyzed via a lateral flow assay, a lateral flow immunoassay, a lateral flow immunochromatographic assay, or a magnetic lateral flow analyzer instrument.

Enumerated embodiment 19. The method of any one of the preceding embodiments, wherein the portion of the magnetic formulation is retrieved using a magnet.

Enumerated embodiment 20. The method of any one of the preceding embodiments, additionally comprising exposing the subject to a magnetic field prior to retrieving at least a portion of the magnetic formulation.

Enumerated embodiment 21. The method of any one of the preceding embodiments, wherein the magnetic field is an oscillating magnetic field.

Enumerated embodiment 22. The method of any one of the preceding embodiments, additionally comprising positioning a magnet on or near a bridge of the subject's nose.

Enumerated embodiment 23. The method of any one of the preceding embodiments, wherein the biological material comprises cerebrospinal fluid, a neural stem cell, a protein, an enzyme, an oligonucleotide, one or more microbes of the patient's microbiome, one or more components of the patient's metabolome, one or more pathogens, and/or one or more biomarkers of interest.

Enumerated embodiment 24. The method of any one of the preceding embodiments, wherein the biological material comprises amyloid-β, a tau protein, or a combination thereof.

Enumerated embodiment 25. The method of any one of the preceding embodiments, wherein the magnetic formulation is delivered via a delivery device comprising a cannula and/or microfluidic channel, wherein the cannula and/or microfluidic channel is configured for insertion into a nasal cavity of the subject.

Enumerated embodiment 26. The method of any one of the preceding embodiments, wherein the formulation is delivered via a device comprising:

a. a housing defining first and second insertable portions, each for insertion into a nasal channel of the subject, wherein, upon insertion of the first insertable portion into the nasal channel of the subject, at least one insertable portion engages tissue within the nasal channel to open or expand an internal nasal valve of the subject thereby positioning at least one of the insertable portions for delivery of the formulation to the olfactory region of the subject or to a sub-region of the nasal cavity of the subject; and b. an actuator which delivers the formulation from either or both of the insertable portions when the device is actuated.

Enumerated embodiment 27. A method of making a diagnosis of a subject, comprising:

a. performing the method of any one of the preceding embodiments, thereby collecting the biological material from the subject;

b. analyzing the collected biological material; and c. based on the analysis of step b., making the diagnosis.

Enumerated embodiment 28. The method of any one of the preceding embodiments, wherein the method is used for diagnosis of Alzheimer's disease or another neurodegenerative disease.

Enumerated embodiment 29. The method of any one of the preceding embodiments, wherein analyzing the biological material comprises identifying and/or quantifying biomarkers, pathogens, and/or microbes in the collected biological material.

Enumerated embodiment 30. The method of any one of the preceding embodiments, further comprising correlating the identified and/or quantified biomarkers, pathogens, and/or microbes with a corresponding physiological characteristic and/or medical condition.

Enumerated embodiment 31. The method of any one of the preceding embodiments, wherein analyzing the biological material comprises using a point-of-care assay system.

Enumerated embodiment 32. The method of any one of the preceding embodiments, wherein the point-of-care assay system is configured to receive a sample of the collected biological material from a delivery device.

Enumerated embodiment 33. A method of delivery of a therapeutic agent to a nasal cavity of a subject, the method comprising:

a. delivering a magnetic formulation to a targeted region of the nasal cavity, the magnetic formulation comprising:

i. a plurality of magnetic particles; and ii. a therapeutic agent; and b. exposing the subject to a magnetic field;

wherein the magnetic field causes movement of the magnetic particles, thereby enhancing delivery of the therapeutic agent.

Enumerated embodiment 34. A method of enhancing contact of a formulation with a targeted region within a nasal cavity of a subject, the method comprising:
- a. delivering a magnetic formulation comprising a plurality of magnetic particles to the targeted region within the nasal cavity; and
- b. causing oscillation or magnetophoretic movement of at least some of the magnetic particles by exposing the subject to a magnetic field, thereby enhancing contact of the magnetic formulation with the targeted region.

Enumerated embodiment 35. The method of any one of the preceding embodiments, wherein the magnetic field is an oscillating magnetic field.

Enumerated embodiment 36. The method of any one of the preceding embodiments, wherein a frequency of the oscillating magnetic field is about 0.01-0.02, about 0.02-0.03, about 0.03-0.04, about 0.04-0.05, about 0.05-0.06, about 0.06-0.07, about 0.07-0.08, about 0.08-0.09, about 0.09-0.1, about 0.1-0.15, about 0.15-0.2, about 0.2-0.25, about 0.25-0.3, about 0.3-0.35, about 0.35-0.4, about 0.4-0.45, about 0.45-0.5, about 0.5-0.55, about 0.55-0.6, about 0.6-0.65, about 0.65-0.7, about 0.7-0.75, about 0.75-0.8, about 0.8-0.85, about 0.85-0.9, about 0.9-0.95, about 0.95-1, about 1-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, about 95-100, about 100-110, about 110-120, about 120-130, about 130-140, about 140-150, about 150-160, about 160-170, about 170-180, about 180-190, about 190-200, about 200-220, about 220-240, about 240-260, about 260-280, about 280-300, about 300-350, about 350-400, about 400-450, about 450-500, about 500-550, about 550-600, about 600-650, about 650-700, about 700-750, about 750-800, about 800-850, about 850-900, about 900-950, or about 950-1000 Hz.

Enumerated embodiment 37. The method of any one of the preceding embodiments, wherein the magnetic field is provided via a permanent magnet.

Enumerated embodiment 38. The method of any one of the preceding embodiments, wherein the magnetic field reduces a necessary residence time for the formulation within the nasal cavity.

Enumerated embodiment 39. A device for delivery of a magnetic formulation to a targeted region of a nasal cavity of a subject and retrieval therefrom, the device comprising:
- a. a housing comprising an insertable portion comprising a distal end, a proximal end, and a retrieval magnet; and
- b. a subject-engaging portion which engages a columella region of the subject to seat the distal end of the insertable portion within an ejection zone of a nasal channel of the subject;

wherein the device is configured to deliver a magnetic formulation to the targeted-region and to retrieve at least a portion of the magnetic formulation from the targeted region.

Enumerated embodiment 40. The device of any one of the preceding embodiments, wherein the targeted region is the olfactory region.

Enumerated embodiment 41. The device of any one of the preceding embodiments, wherein the device comprises a magnetic portion for retrieval of a portion of the magnetic formulation.

Enumerated embodiment 42. The device of any one of the preceding embodiments, wherein the device dispenses the magnetic formulation as a laminar jet.

Enumerated embodiment 43. The device of any one of the preceding embodiments wherein the device comprises a compliant dispensing tip comprising a compliant and flexible soft nib.

Enumerated embodiment 44. The device of any one of the preceding embodiments, wherein application of pressure by the subject-engaging portion to the columella region of the subject enables and/or causes delivery of the formulation to the subject from the insertable portion.

Enumerated embodiment 45. The device of any one of the preceding embodiments, wherein the insertable portion comprises a dispensing element for delivery of the magnetic formulation to the targeted sub-region of the subject.

Enumerated embodiment 46. A device for retrieval of magnetic particles from a nasal cavity of a subject, the device comprising:
- a. a retrieval magnet; and
- b. a magnet support, configured to position the retrieval magnet within a targeted region of the nasal cavity so as to facilitate retrieval of a plurality of magnetic particles from the targeted region.

Enumerated embodiment 47. A system for enhancing contact of a formulation with a targeted region within a nasal cavity of a subject, the system comprising:
- a. a device for delivery of a magnetic formulation comprising a plurality of magnetic particles to the targeted region of the nasal cavity; and
- b. a magnet for causing movement of the magnetic formulation within the nasal cavity, thereby enhancing contact with the targeted region.

Enumerated embodiment 48. The system of any one of the preceding embodiments, additionally comprising a support configured to hold the magnet at a desired position on or near a bridge of a subject's nose.

Enumerated embodiment 49. The system of any one of the preceding embodiments, additionally comprising a retrieval magnet configured to be inserted within a nasal cavity of a subject for retrieval of a portion of the magnetic formulation.

Enumerated embodiment 50. The system of any one of the preceding embodiments, wherein the retrieval magnet has a diameter of about 2.5 mm.

Enumerated embodiment 51. The system of any one of the preceding embodiments, additionally comprising a retrieval magnet configured to be positioned outside a nasal cavity of a subject for retrieval of a portion of the magnetic formulation.

Enumerated embodiment 52. A magnetic formulation for biomarker sampling from the nasal cavity of a subject, the formulation comprising a plurality of magnetic particles and configured to capture biological material once delivered within the nasal cavity, wherein the delivered formulation is configured to be withdrawn from the nasal cavity with the biological material.

Enumerated embodiment 53. The formulation of any one of the preceding embodiments, wherein the magnetic particles are coated with tau antibodies, beta-amyloid antibodies, or a combination thereof.

Enumerated embodiment 54. The formulation of any one of the preceding embodiments, wherein the magnetic particles comprise a first plurality of magnetic particles, coated with tau antibodies, and a second plurality of magnetic particles, coated with beta-amyloid antibodies.

Enumerated embodiment 55. The formulation of any one of the preceding embodiments, wherein the magnetic particles have an average diameter of about 50 micrometers.

Enumerated embodiment 56. The formulation of any one of the preceding embodiments, wherein the magnetic particles have an average diameter of about 0.01-0.015, about 0.015-0.02, about 0.02-0.025, about 0.025-0.03, about 0.03-0.035, about 0.035-0.04, about 0.04-0.045, about 0.045-0.05, about 0.05-0.055, about 0.055-0.06, about 0.06-0.065, about 0.065-0.07, about 0.07-0.075, about 0.075-0.08, about 0.08-0.085, about 0.085-0.09, about 0.09-0.095, about 0.095-0.1, about 0.1-0.15, about 0.15-0.2, about 0.2-0.25, about 0.25-0.3, about 0.3-0.35, about 0.35-0.4, about 0.4-0.45, about 0.45-0.5, about 0.5-0.55, about 0.55-0.6, about 0.6-0.65, about 0.65-0.7, about 0.7-0.75, about 0.75-0.8, about 0.8-0.85, about 0.85-0.9, about 0.9-0.95, about 0.95-1, about 1-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, about 95-100, about 100-105, about 105-110, about 110-115, about 115-120, about 120-125, about 125-130, about 130-135, about 135-140, about 140-145, about 145-150, about 150-155, about 155-160, about 160-165, about 165-170, about 170-175, about 175-180, about 180-185, about 185-190, about 190-195, about 195-200, about 200-210, about 210-220, about 220-230, about 230-240, about 240-250, about 250-260, about 260-270, about 270-280, about 280-290, about 290-300, about 300-320, about 320-340, about 340-360, about 360-380, about 380-400, about 400-420, about 420-440, about 440-460, about 460-480, or about 480-500 micrometers.

Enumerated embodiment 57. The formulation of any one of the preceding embodiments, wherein the formulation is delivered to the olfactory region of the nasal cavity.

Enumerated embodiment 58. The formulation of any one of the preceding embodiments, wherein the formulation is configured to capture biological material from a targeted sub-region of the nasal cavity.

Enumerated embodiment 59. The formulation of any one of the preceding embodiments, wherein the delivered formulation is configured to preserve the captured biological material when being withdrawn.

Enumerated embodiment 60. The formulation of any one of the preceding embodiments, wherein the biological material comprises cerebrospinal fluid (CSF), one or more microbes of the patient's microbiome, one or more components of the patient's metabolome, one or more pathogens, and/or one or more biomarkers of interest.

Enumerated embodiment 61. The formulation of any one of the preceding embodiments, wherein the formulation is configured to capture specific biological material.

Enumerated embodiment 62. The formulation of any one of the preceding embodiments, wherein the formulation comprises a buffered saline solution, a polyethylene glycol, a glycerol, or a combination thereof.

Enumerated embodiment 63. The formulation of any one of the preceding embodiments, wherein the buffered saline solution is 100 mM phosphate buffered saline.

Enumerated embodiment 64. The formulation of any one of the preceding embodiments, wherein the formulation comprises one or more gelling agents and/or thickeners.

Enumerated embodiment 65. The formulation of any one of the preceding embodiments, wherein the formulation comprises a viscosity between about 20-40 cP.

Enumerated embodiment 66. The formulation of any one of the preceding embodiments, wherein the formulation comprises a viscosity between about 0-5, about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 80-85, about 85-90, about 90-95, or about 95-100 cP.

Enumerated embodiment 67. The formulation of any one of the preceding embodiments, wherein the formulation comprises a viscosity between about 100-110, about 110-125, about 125-150, about 150-200, about 200-250, about 250-300, about 300-350, about 350-400, about 400-450, about 450-500, about 500-550, about 550-600, about 600-650, about 650-700, about 700-750, about 750-800, about 800-850, about 850-900, about 900-950, or about 950-1000 cP.

Enumerated embodiment 68. The formulation of any one of the preceding embodiments, wherein the formulation comprises a viscosity modifier to provide a desired viscosity for the formulation.

Enumerated embodiment 69. The formulation of any one of the preceding embodiments, wherein the viscosity modifier comprises at least one of glycerol, pectin, and polyethylene glycol.

Enumerated embodiment 70. The formulation of any one of the preceding embodiments, wherein the viscosity modifier comprises 25-75% of the formulation by volume.

Enumerated embodiment 71. The formulation of any one of the preceding embodiments, wherein the formulation is configured for removal from the nasal cavity using a magnet.

Enumerated embodiment 72. The formulation of any one of the preceding embodiments, wherein the formulation comprises one or more specific mono or polyclonal antibodies so as to target a specific biological material.

Enumerated embodiment 73. The formulation of any one of the preceding embodiments, wherein the formulation comprises one or more specific aptamers so as to target a specific biological material.

Enumerated embodiment 74. The formulation of any one of the preceding embodiments, wherein the formulation is provided, delivered, and/or withdrawn as a bolus of the formulation.

Enumerated embodiment 75. A magnetic formulation for delivery of a therapeutic agent to a targeted region of a nasal cavity of a subject, the formulation comprising a magnetic formulation comprising a plurality of magnetic particles and a therapeutic agent, wherein the magnetic particles are configured to enhance contact of the therapeutic agent with the targeted region.

Enumerated embodiment 76. The formulation of any one of the preceding embodiments, wherein the formulation is delivered to the olfactory region of the nasal cavity.

Enumerated embodiment 77. A method of collecting biological material from a targeted region of a subject, the method comprising:
a. delivering a magnetic formulation comprising a plurality of magnetic particles to the targeted region of a subject, wherein the magnetic formulation is configured to capture the biological material; and
b. retrieving at least a portion of the magnetic formulation from the targeted region, thereby collecting any biological material captured by the portion of the magnetic formulation.

Enumerated embodiment 78. The method of any one of the preceding embodiments, wherein the targeted region is a rectal region, a vaginal region, a subregion of an ear, a navel, a skin subregion, or another body surface or orifice.

What is claimed is:

1. A method of collecting biological material from a targeted region of a nasal cavity of a subject, the method comprising:
a) delivering a formulation comprising a plurality of magnetic particles to the targeted region of the subject, wherein the plurality of magnetic particles is configured to capture the biological material;
b) exposing the subject to an oscillating magnetic field, the magnetic field configured to:
(i) promote mixing of the plurality of magnetic particles within the formulation; and
(ii) promote mixing of the formulation within the targeted region, thereby promoting capture of the biological material; and
c) retrieving at least a portion of the plurality of magnetic particles from the targeted region, thereby collecting any biological material captured by the portion of the plurality of magnetic particles.

2. The method of claim 1, wherein the targeted region is an olfactory region, a nasal turbinate, a nasopharynx, a sub-region of a nasal lymphatic system, or a sub-region of the nasal cavity of the subject.

3. The method of claim 1, wherein the biological material is captured from cerebrospinal fluid (CSF).

4. The method of claim 1, wherein the biological material comprises cerebrospinal fluid, a neural stem cell, a protein, an enzyme, an oligonucleotide, one or more microbes of the patient's microbiome, one or more components of the patient's metabolome, one or more pathogens, and/or one or more biomarkers of interest.

5. The method of claim 1, wherein the collected biological material comprises amyloid-ß, a tau protein, or a combination thereof.

6. The method of claim 1, wherein the magnetic particles are coated with or coupled to one or more antibodies configured to bind to a selected biological material.

7. The method of claim 1, wherein the portion of the plurality of magnetic particles is retrieved using a magnet.

8. The method of claim 1, wherein a frequency of the oscillating magnetic field is about 0.1-10 Hz.

9. The method of claim 1, wherein the magnetic field reduces a residence time for the formulation within the nasal cavity.

10. The method of claim 1, wherein the formulation is delivered and/or withdrawn as a bolus of the formulation.

11. The method of claim 1, further comprising analyzing the biological material using a point-of-care assay system.

12. The method of claim 1, wherein exposing the subject to the magnetic field comprises positioning a magnet on or near a bridge of the subject's nose.

13. A method of collecting biological material from a targeted region of a nasal cavity of a subject, the method comprising:
inserting a device comprising a housing comprising an insertable portion for insertion into a nasal channel of the subject, configured such that upon insertion into the nasal channel of the subject, the insertable portion engages tissue within the nasal channel to open or expand an internal nasal valve of the subject;
actuating the device;
delivering a formulation comprising a plurality of magnetic particles to the targeted region of a subject, the plurality of magnetic particles configured to capture the biological material;
exposing the subject to an oscillating magnetic field, the magnetic field configured to: (i) promote mixing of the plurality of magnetic particles within the formulation; and (ii) promote mixing of the formulation in the targeted region, thereby promoting capture of the biological material; and
retrieving at least a portion of the plurality of magnetic particles from the targeted region,
thereby collecting any biological material captured by the portion of the plurality of magnetic particles.

* * * * *